United States Patent
Wadhwa et al.

(10) Patent No.: US 6,670,450 B1
(45) Date of Patent: Dec. 30, 2003

(54) PROTEIN AND GENE INVOLVED IN MYOCYTE DIFFERENTIATION

(75) Inventors: Renu Wadhwa, Niihari-mura (JP); Sunil C. Kaul, Tsukuba (JP); Roger R. Reddel, Westmead (AU)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/684,579

(22) Filed: Oct. 6, 2000

Related U.S. Application Data

(63) Continuation-in-part of application No. PCT/JP99/01913, filed on Apr. 9, 1999.

(30) Foreign Application Priority Data

Apr. 10, 1998 (JP) ............................................. 10-115975

(51) Int. Cl.$^7$ ........................... C07K 1/00; C07K 14/00; C07K 17/00
(52) U.S. Cl. ....................................................... 530/350
(58) Field of Search .......................................... 530/350

(56) References Cited

PUBLICATIONS

Doerks (1998) TIG 14(6):248–250.*
Aldrich et al. (1994) Cell 79:649–658.*
Wadhwa, R. et al., "Cloning and characterization of a Novel Gene, striamin, That Interacts with the Tumor Suppressor Protein p53*", *J. Biol. Chem.*, 274:14948–14955, 1999.
Soddu, S. et al., "Interference with p53 Protein Inhibits Hematopoietic and Muscle Differentiation", *J. Cell Biol.*, 134:193–204, 1996.
Puri, P.L. et al., "Uncoupling of p21 Induction and MyoD Activation Results in the Failure of Irreversible Cell Cycle Arrest in Doxorubicin–Treated Myocytes", *J. Cell. Biochem.*, 66:27–36, 1997.
Cerone, M.A. et al., "p53 is Involved in the Differentiation But Not in the Differentiation–Associated Apoptosis of Myoblasts", *Cell Death and Differentiation*, 7:506–508, 2000.
Liu, C. et al., "MyoD–Dependent Induction During Myoblast Differentiation of p204, a Protein Also Inductible by Interferon", *Cell. Biol.*, 20:7024–7036, 2000.
Perry, R.L. et al., "Molecular Mechanisms Regulating Myogenic Determination and Differentiation", *Front. Biosci.*, 5:750–767, 2000.
White, J.D. et al., "Myotube Formation is Delayed but not Prevented in MyoD–deficient Skeletal Muscle: Studies in Regenerating Whole Muscle Grafts of Adult Mice", *J. Histochem. Cytochem.*, 48:1531–1543, 2000.
Puri, P.L. et al., "Regulation of Muscle Regulatory Factors by DNA–binding, Interacting Proteins, and Post–Transcriptional Modifications", *J. Cell. Physiol.*, 185:155–173, 2000.
Tintignac, L. et al., "Concise Explanation of the French Reference", *Bull. Cancer*, 87:521, 2000 (Attached a Concise Explanation of the French Reference).
Olson, E.N. et al., "bHLH factors in Muscle Development: Dead Lines and Commitment, What to Leave in and What to Leave Out", *Genes & Dev.*, 8:1–8, 1994.
Weintraub, H. et al., "The myoD Gene Family: Nodal Point During Specification of the Muscle Cell Lineage", *Science*, 251:761–766, 1991.
Emerson, C.P. jr., "Skeletal Myogenesis: Genetics and embryology to the Fore", *Curr. Opin. Genet. Dev.*, 3:265–274, 1993.
Shiio, Y. et al., "Activation of the Retinoblastoma Gene Expression by Bcl–3: Implication for Muscle Cell Differentiation", *Oncogene*, 12:1837–1845, 1996.
Wang, J. et al., "Rb Functions to Inhibit Apoptosis During Myocyte Differentiation[1]", *Cancer Research*, 57:351–354, 1997.
Guo, K. et al., "MyoD–Induced Expression of p21 Inhibits Cyclin–Dependent Kinase Activity upon Myocyte Terminal Differentiation", *Cell Biol.*, 15:3823–3829, 1995.
Kiess, M. et al., "Expression of the Positive Regulator of Cell Cycle Progression, Cyclin D3, is Induced During Differentiation of Myoblasts into Quiescent Myotubes", *Oncogene*, 10:159–166, 1995.
Song, K.S. et al., "Expression of Caveolin–3 in Skeletal, Cardiac, and Smooth Muscle Cells", *Biol. Chem.*, 271:15160–15165, 1996.
Kostrominova, T.Y. et al., "Temporal and Spatial Appearance of α–Dystroglycan in Differentiated Mouse Myoblasts in Culture", *J. Cell. Biochem.*, 58:527–534, 1995.
Takagi, H. et al., "Overexpression of DNA Methyltransferase in Myoblast Cells Accelerates Myotube Formation", *Eur. J. Biochem.*, 231:282–291, 1995.
Wadhwa, R. et al., "Protein Markers for Cellular Mortality and Immortality", *Mutat. Res.*, 256:243–254, 1991.
Rabbitts, T.H. et al. "fusion of the dominant Negative Transcription Regulator CHOP with a Novel Gene FUS by Translocation t(12;16) in Malignant Liposarcoma", *Nat. Genet.*, 4:175–180, 1993.

(List continued on next page.)

*Primary Examiner*—Christina Chan
*Assistant Examiner*—Michail Belyavskyi
(74) *Attorney, Agent, or Firm*—Fish & Richardson P.C.

(57) ABSTRACT

A gene was unexpectedly isolated in an attempt to isolate a gene specifically expressed in immortalized cells via antibody screening using an antibody raised against a protein occurring specifically in immortalized cells. The gene thus isolated shares no sequence homology with the entries deposited in the database and was strongly expressed in skeletal muscles and undifferentiated cells. The protein encoded by this gene inhibits the differentiation of myoblasts into myotubes. It also inhibits the transactivation function of p53, a transcription factor involved in tumor suppression.

6 Claims, 11 Drawing Sheets

PUBLICATIONS

Kuroda, M. et al., "Chimeric TLS/FUS–CHOP Gene Expression and the Heterogeneity of its Junction in Human Myxoid and Round Cell Liposarcoma", *J. Pathol.*, 147:1221–1227, 1995.

Blake, D.J. et al., G–Utrophin, the Autosomal Homologue of Dystrophin Dp116, is Expressed in Sensory Ganglia and Brain, *Proc. Natl. Acad. Sci. USA.*, 92:3697–3701, 1995.

Love, D.R. et al., "An Autosomal Transcript in Skeletal Muscle with Homology to Dystrophin", Nature, 339:55–58, 1989.

* cited by examiner

FIG. 1

```
         5'-GCAGGTCTGAGTTCAAGGACAGCCTGGTCTACGCATTGAGTTCTAGAACAGCCAAGGCTACACAAAGA      68
ATCCCTGTCTTAAAAAACAAAAACAAATAAAAAACAAACAAACAAAAAACAAAACAAAACAAAAACAACAAAAAGACCA   147
ATGGGGAAAAAAGAAAGAAAAAACAAGAAAAGAAAAAAGAATAGCTTCCCTGTTCTCTGCAGGGTAGTTTTAGTAATG   226
AATGCTCAAAGCTCCACAGTCTATGGCACCCAAGTGGTATTCTTATATTGTTTGCAACTAACTATCC ATG AAA GGC   302
                                                                    M   K   G     3
CTG GCT GGC GAG TGG CAT CAG GAC TCT GGC CTA GAC ATC AGG GAG AAG GCA GAA GAC TTC   362
 L   A   G   E   W   H   Q   D   S   G   L   D   I   R   E   K   A   E   D   F    23
TCC CTG CCC TGG CTG CTG CCT AGA TTG ATG GCC TTA GTC ATG CAG GAA GAA GGA AGG TTC   422
 S   L   P   W   L   L   P   R   L   M   A   L   V   M   Q   E   E   G   R   F    43
AGA AGT GAC AGG AAT CAT GGG TAT TTA AGG GAA TGG CTT AGG ATT CAG GCA CTG ACA GCT   482
 R   S   D   R   N   H   G   Y   L   R   E   W   L   R   I   Q   A   L   T   A    63
TGT CTG CCT TCC CCT CTG GGG AGG GTC CAC TAT GCC CAG TGT TCA CCG AAA CAA AAA GGA   542
 C   L   P   S   P   L   G   R   V   H   Y   A   Q   C   S   P   K   Q   K   G    83
AGG CTG CCA AGA GGC TGG GCT TCT CTG CCA TCC CTA AGT GTG CTT GTC AGG GCT CTG AGA   602
 R   L   P   R   G   W   A   S   L   P   S   L   S   V   L   V   R   A   L   R   103
GCG TCT AAC GCT TTC TCA CTC GGG AAC TAC TAC TGC TGT CCG TGG AGG GGG ACA AGA TGG   662
 A   S   N   A   F   S   L   G   N   Y   Y   C   C   P   W   R   G   T   R   W   123
GCC AAA GGG CAG CCG GGA GAG TGG GCA AGG CCA AGG GCG AGC TCA CCT TCT GCG CAC CGA   722
 A   K   G   Q   P   G   E   W   A   R   P   R   A   S   S   P   S   A   H   R   143
GAA GGC GTG GCA GTG ACA TGA AAC ATT AGG TCA CAT GGC CTT CCC CTC CGG CCT TAG CGT   782
 E   G   V   A   V   T   *                                                        149
GCCTACACATCTGCACAGAGAAGGAGAAGAGGTTGAGGAGAGAATAGAGCAGTACAGAGCCAACTCAAACAGCAGCAGC   861
AGACAGAGAGCACGAGACAGAAGGTGAGGGCGCAGGAGGAGAGGAGCGGGCCAGAAGGGACAGTGAGCAGACAGGGAAA   940
TGAGCAAGGGAGGCAGGGGTGGGGGCAGAACCTCCCCATCATGCACTTCCGACAGGTCACTCAGAGGTCACGAGGAACAT  1019
GTGGCAGGCCTAGGGACCAAAGCCATGAAGGTTTCTGTGGTCACAGCCATGTGCTGCTTCTGGGAGGGACATCTGCTGC  1098
CCTAGTTAAGCATGGTAGTGAGTGACAACTTTGGGTTTTCCAATGCCCACAGCAGGAACCGGACCTGGCTTTATACCCT  1177
CTGCCTCCCAGAGCATTCTGGGCCAGGGTACCAGAAGGGGCCTCACTGCCGCTTATATCCTCTCCCCTCCTCCCACAGG  1256
CCATGCTGTCTAAGAACACAGTGGACAGTGGCCACATGGGATCCCAAGCAGGACAGGGCTCAAGGCTGGAGACAGACT  1335
TGTTAAATCGTGCCTGAGGGGGAAGGTATATGACACCTTTGCAAACTGGGTAAGTGAAGAGAGGAAGTGTACGACAGCC  1414
CAACGGAAGCCCCCCTCCCCCCCAGTACTGTGAAGCCTGTCAATCCCACAGGGGTGGGACTTCGGCTTACGGTCTCCTG  1493
CAACCAGGACCTTTCACACACCCCACCCTTCTGCCTGGGTCATGTAGCTGATCCCAGAGGACTAGCACTTTATGTTTTC  1572
AGTACTGATGGATGGTAAGAGACAGCAGAATTGCTGAGTTATGGAGGAGGCAAACAAGACCTCTTCAGAAACACAGCTA  1651
ACTACCCACAAGACCAGAACCAGGCTGTCCAGACCCCTGCACTGGAACATGGAGGGATGGAACGGTCAGGGAGGGGGC   1730
AGGAGCATGGCTAGGATCTGGCATGAGGTGTGCTGGGCATAGAAGGAGTAGGGGCCCCAGGTAGGTTCTGGGCTCAGAG  1809
AAGGCATGATAGAAGCTAGACACATAAGTCATAATGGCTTTCTCATCTGGCCGGGCAGTTTCGACGATGCTTCAGCATC  1888
CAGCATTTTAGGGATGTCCAGGGAACCTCTCTGCCACATCATAGCCGTGTTCAGTTGTGAGTAAGGATCATCCTAAAGA  1967
GAAGCACCAAGTGAGCCTACAGAGAGGACACAGGTCACAGTCGATTCGGAGATGGGAGGTGTGTGTGTGTGTGTGTGTG  2046
TGTGTGTGTGTGTGTGTGTGTGTACCAGCCCTTCTCAGGTTCTAGGTAAGAAAGGGTGACTTCAAGGCCTTTTTTAGGG  2125
GTCACTAGTTAGAGGTTTGAAACATTCTCTTCCCCCATCACTCTTCAGTATGGAAATGGGGGAAGAGAATACATAGGCC  2204
TGATGTTAGAGTTGGAGTAGGAAAGAACTAAGAAGTGGGGTTGAGAGCCATCAGTTCTGGCAGGAGACATGGGTAAATC  2283
GACTCAGACTTAGTCCCCCCCCCCCCCCCTGTCTGAACTCAATAGTTGGGATAGGTGCTCTTAACTCATAAAGATTA   2362
GTGAGAAGTTGAAGCTGACCCACCATGGATTCCCATGTGTTGGGTTATTCTAAGTAGCCATGGCTTTTTTAGTGGCCTC  2441
TGTGATCTTTTCTCGAAAGCTAAATGGGGAGAGCTGGCAAAGGATGTTGGGGACTCTGGGATCCTTGCATCCCGGAGTG  2520
TACTTCAAACATGGAGGTAATGTAAAATGGAGTTAGGTGCCTCCTCAGCCCAGCAGGCCACACTGCTCAGTCAGTCTCA  2599
TAAGATGGTGCGGCTGCTGTGGAGGGCGGCATGGAGGGTCCCCAAAAAGTTATACTCCTGCATAAGGCCCAGGGATTAT  2678
T-3'                                                                            2679
```

Figure 5
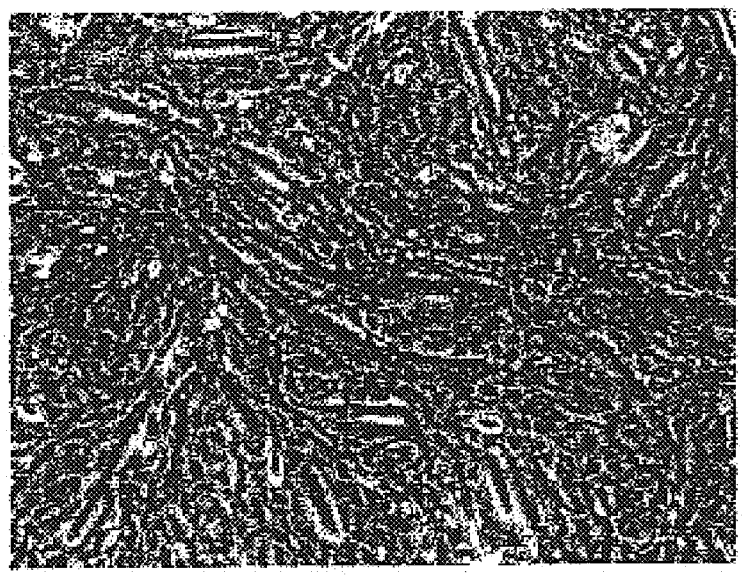
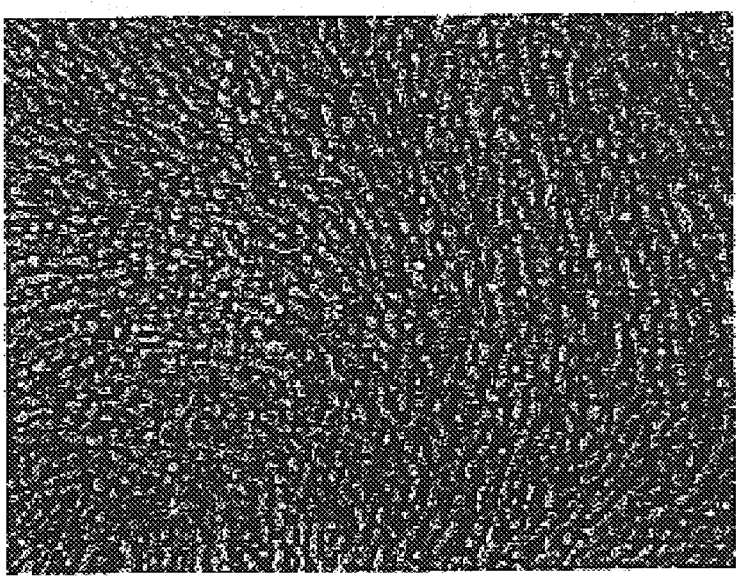

FIG. 11
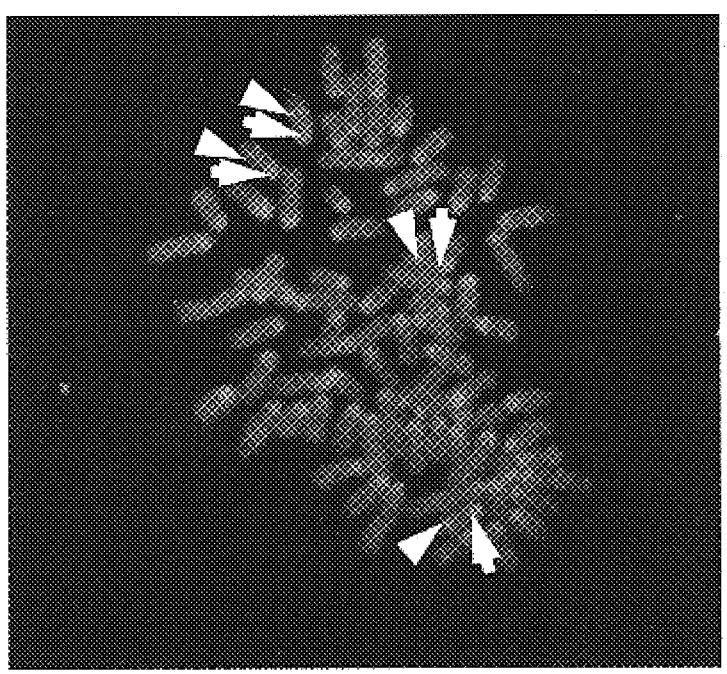 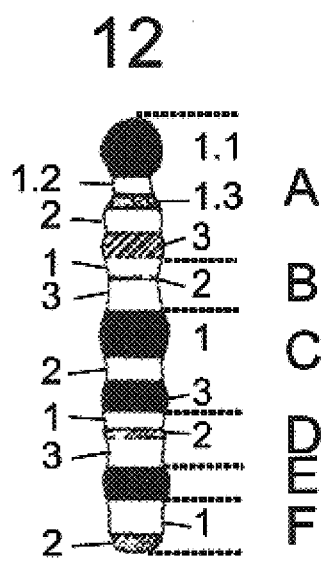

US 6,670,450 B1

PROTEIN AND GENE INVOLVED IN MYOCYTE DIFFERENTIATION

CROSS-REFERENCE TO RELATED APPLICAITONS

This application is a continuation-in-part of PCT/JP99/01913, filed Apr. 9, 1999 and claims priority from Japanese Application 10/115975, filed Apr. 10, 1998.

TECHNICAL FIELD

The present invention relates to a novel protein involved in myocyte differentiation and DNA encoding the protein.

BACKGROUND OF THE INVENTION

Genes, such as muscle creatine kinase, troponin, caveolin 3, α-actin, and myosin, are reported to be expressed predominantly in the skeletal muscles. A family of transcription factors specifically expressed in the muscles, including myoD, myogenin, myf-5, and MRF-4/herculin/myf-6, have been cloned. These factors are phosphorylated nuclear proteins containing a helix-loop-helix (bHLH) motif, as required for both dimerization and DNA binding, and are believed to be determinants of the cell-specific differentiation program (Olson and Klein (1994), Genes & Dev. 8:1–8). When one of these factors is introduced into non-myogenic cells, differentiation into mature muscle cells is initiated (Weintraub et al. (1991), Science 251:761–766). The myoD family, a group of transcription factors, has been found to direct muscle formation, inhibit proliferation, activate differentiation and induce a contractile phenotype. While myoD and myf-5 are expressed within the proliferating myoblasts, myogenin and MRF-4 are not expressed until the myoblasts withdraw from the cell cycle in response to mitogen withdrawal. Based on these findings, it was demonstrated that myogenin and MRF-4 activate and maintain the expression of muscle-specific genes (Emerson (1993), Curr. Opin. Genet. Dev. 3:265–274), while myoD and myf-5 are thought to play a role in the proliferation of myoblasts. Other cell-cycle regulatory proteins, such as RB (Shiio et al. (1996), Oncogene 12:1837–1845, Wang et al. (1997), Cancer Research 57:351–354), p21 (Guo et al. (1995), Mol. Cell Biol. 15:3823–3829), cyclin D, cdk2, cdk4 (Kiess et al. (1995), Oncogene 10:159–166) and tumor suppressor gene p53 (Soddu et al. (1996), J. Cell Biol. 134:193–204) are involved in the muscle cell differentiation program. Recently, caveolin 3 (Song et al. (1996), J. Cell Biol. 271:15160–15165), α-dystroglycan (Kostrominova and Tanzer (1995), J. Cell Biochem. 58:527–534) and DNA methyltransferases (Takagi et al. (1995), Eur. J. Biochem. 231:282–291) have been shown to play positive roles in myogenic differentiation.

SUMMARY OF THE INVENTION

An objective of the present invention is to provide a novel protein and gene involved in myocyte differentiation, and the production and use thereof.

The inventors carried out an antibody screening, using an antibody raised against a protein specific to immortalized cells, to isolate genes specifically expressed in the immortalized cells. Unexpectedly, a novel gene was isolated, which was not an initial objective gene. By analyzing the isolated gene, the inventors found that this gene is a novel gene showing no significant homology with any known genes deposited in the database, and is strongly expressed in skeletal muscle and undifferentiated cells. The inventors also analyzed the protein encoded by the gene, and found that the protein has an inhibitory effect on the differentiation of myoblasts into myotubes. The inventors also found that the protein interacts with p53, a transcription factor involved in tumor suppression, to inhibit the p53 transactivation function.

The present invention relates to a novel protein having an inhibitory effect on the differentiation of myoblasts into myotubes, and the gene encoding the protein, and the production and the use thereof. More specifically the present invention relates to:

(1) a protein comprising the amino acid sequence of SEQ ID NO:1, or a protein comprising said amino acid sequence in which one or more amino acids are substituted, deleted or added and exhibiting an inhibitory effect on the differentiation of myoblasts into myotubes;

(2) a protein encoded by DNA that hybridizes with the DNA comprising the nucleotide sequence of SEQ ID NO:2, wherein said protein exhibits an inhibitory effect on the differentiation of myoblasts into myotubes;

(3) a DNA encoding the protein according to (1);

(4) a DNA hybridizing with the DNA comprising the nucleotide sequence of SEQ ID NO:2, wherein said DNA encodes a protein exhibiting an inhibitory effect on the differentiation of myoblasts into myotubes;

(5) a vector containing the DNA according to (3);

(6) a transformant retaining the DNA according to (3) in an expressible manner;

(7) a method for producing the protein according to (1) or (2), said method comprising culturing the transformant according to (6);

(8) an antibody binding to the protein according to (1) or (2);

(9) a method of screening for a compound that binds to the protein according to (1) or (2), said method comprising the steps of:
  a) contacting a test sample with said protein or a partial peptide thereof;
  b) detecting the binding activity of the test sample to said protein or a partial peptide thereof; and
  c) selecting a compound binding to said protein or a partial peptide thereof;

(10) a compound, binding to the protein according to (1) or (2), wherein said compound can be isolated using the method according to (9);

(11) a method of screening for a compound that promotes or inhibits the activity of the protein according to (1) or (2), the method comprising the steps of:
  a) contacting myoblasts with said protein in the presence of a test sample;
  b) detecting the differentiation of the cells into myotubes; and
  c) selecting a compound which can increase or decrease the inhibitory activity of the protein, compared with its inhibitory activity as detected in the absence of said test sample;

(12) a method of screening for a compound that promotes or inhibits the activity of the protein according to (1) or (2), said method comprising the steps of:
  a) providing p53-deficient cells with a vector expressing said protein, a vector expressing p53, and a vector expressing a reporter gene in response to p53;
  b) contacting a test sample with said cells;
  c) detecting the reporter activity in said cells; and d) selecting a compound that can reduce or increase the reporter activity compared with the activity in the cells without contact with said test sample (control);

(13) a compound that promotes or inhibits the activity of the protein according to (1) or (2), wherein said compound can be isolated using the method according to (11) or (12); and

(14) a DNA comprising at least 15 nucleotides in length and specifically hybridizing with the DNA comprising the nucleotide sequence of SEQ ID NO:2.

The present invention relates to a novel protein, "striamin," that inhibits the differentiation of myoblasts into myotubes. (The inventors initially designated the protein "striatin" in the original application (Japanese Patent Application No. Hei 10-115975), but another protein was later found to have the same name; hence the renaming to "striamin"). The nucleotide sequence of striamin cDNA derived from mouse DNA is shown in SEQ ID NO:1, and the amino acid sequence of the protein encoded by the cDNA is shown in SEQ ID NO:2. As shown in SEQ ID NO:1, mouse striamin cDNA has an ORF encoding a protein of 149 amino acids. As determined by immunoprecipitation of the striamin protein translated in vitro (FIG. 2A), and by Western blotting of the recombinant striamin protein (FIG. 2B), the mouse-derived striamin protein has a molecular weight of about 18 kDa. Northern blot analysis showed that the striamin gene is expressed in the undifferentiated cells, and that the expression of this gene is inhibited during myoblast differentiation into myotubes (FIG. 4C). Overexpression of the gene actually blocked the differentiation of myoblasts into myotubes (FIG. 5). These facts suggest that the striamin protein is involved in the duration of the undifferentiated state of the cells.

The expression of the striamin protein also inhibited expression of the p53 transactivation function. The expression of this transcription factor is known to be upregulated during muscle differentiation (FIG. 7 and FIG. 8). The striamin protein was further shown to interact with p53 both in vivo and in vitro (FIG. 9 and FIG. 10). It is reported that p53 activity increases substantially in the process of muscle formation in vitro. Inhibition of p53 activity by striamin is quite consistent with the down-regulation of striamin during myogenesis. These facts suggest that striamin affects muscle formation through direct interaction with p53.

The striamin protein of the present invention may be prepared as a recombinant protein by making use of recombinant technology, and as a naturally occurring protein. For example, a recombinant protein can be prepared, as described below, by culturing cells transformed with DNA encoding the striamin protein. In addition, a naturally occurring protein can be isolated from tissues, such as skeletal muscles, using methods known by a person skilled in the art, for example, by performing affinity chromatography using an antibody that binds to the striamin protein as described below. The antibody may be a polyclonal or monoclonal antibody. Polyclonal antibodies can be prepared, for example, by obtaining serum from a small animal, such as a rabbit, that is immunized with the striamin protein, followed by purification using, for example, ammonium sulfate precipitation, protein A column, protein G column, DEAE ion exchange chromatography, and striamin protein coupled affinity column. Monoclonal antibodies can be prepared as follows. A small animal, such as a mouse, is immunized with the striamin protein. The mouse is then dissected to remove the spleen, which is subsequently homogenized to dissociated cells. These are then fused to mouse myeloma cells using a reagent such as polyethylene glycol, and the fused cells (hybridomas) thus obtained are subjected to the selection of clones producing antibodies against the protein. Subsequently, a hybridoma cell thus obtained is transplanted into a mouse intraperitoneally, and the ascites fluid is recovered from the mouse, followed by purification using, for example, ammonium sulfate precipitation, protein A column, protein G column, DEAE ion exchange chromatography, and striamin protein coupled affinity column.

When the antibody obtained is for human use (e.g., for antibody therapy), a humanized or human antibody is advantageous to reduce the immunogenicity. Among methods for humanizing antibodies, the CDR grafting method is well known. In this method, the antibody gene is cloned from the cell producing the monoclonal antibody and its antigen determinant portion is grafted to an existing human antibody. Alternatively, human antibodies can be prepared directly, by the same method used for conventional monoclonal antibodies, i.e., by immunizing a mouse whose immune system is replaced with a human's immune system.

In addition, as well as preparing a native striamin protein, one skilled in the art can prepare modified proteins whose functions are equivalent to those of the native protein (e.g., an inhibitory effect on the differentiation of myoblasts into myotubes, binding activity to p53, an inhibitory effect on the p53 transactivation function), using a well-known method for modifying proteins, such as for substitution of amino acid residues in the protein. Spontaneous mutation of an amino acid in the protein may possibly occur. Thus, the proteins of the present invention include mutant proteins whose amino acid sequences differ from that of the native protein by amino acid substitution, deletion and/or addition, and whose function is equivalent to the native protein. The methods for modifying amino acids, which are well-known to one skilled in the art, include the site-directed mutagenesis system by PCR (GIBCO-BRL, Gaithersburg, Md.), the site-directed mutagenesis method using oligo-nucleotides (Kramer, W. and Fritz, H. J. (1987), Methods in Enzymol., 154:350–367), and Kunkel's method (Methods in Enzymol. (1988), 85:2763–2766). Amino acid substitutions are made at typically 10 or less residues, preferably six or less residues and more preferably three or less residues.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Any inhibitory effect of the proteins thus prepared on the differentiation of myoblasts into myotubes can be detected using, for example, a method such as that for determining differentiation potency by using cultured mouse C2C12 myoblast cell line. (When cultured in serum-free DMEM medium or DMEM medium containing 2% equine serum, mouse C2C12 myoblast cell line is differentiated into multinucleate myotube cells.) In this method, a C2C12 myoblast cell line is cultured in the presence of a test protein to determine the potency of the differentiation into multinucleate myotube cells (See Example 6). Binding of the prepared protein to p53 can be detected, for example, by contacting the two proteins in vitro or in vivo, which are then subjected to immunoprecipitation with an anti-p53 antibody, an antibody against the prepared protein or, if a tag is added to either protein, an antibody against the tag, and subsequently by Western blotting (see Examples 10 and 11). Inhibition of p53 transactivation by the prepared protein can be detected, for example, by determining the reporter activity of the cells into which both a vector expressing p53 and a vector carrying a p53-responsive reporter, and subsequently a vector expressing the prepared protein, are introduced. Reporter activity is then compared with that of a control, i.e., cells not harboring the vector expressing the prepared protein (See Examples 8 and 9).

It is also well within the art of a person with ordinary skill to obtain a protein functionally equivalent to the mouse striamin protein (SEQ ID NO:2) by isolating DNA showing significant homology with the DNA that encodes the mouse striamin protein (SEQ ID NO:1) or a part thereof, using technology such as a hybridization technique (Sambrook et al., Molecular Cloning 2nd ed. 9.47–9.58, Cold Spring Harbor Lab. Press, 1989). Thus, the proteins of the present invention also include those proteins that are encoded by DNA hybridizing with the DNA encoding the mouse striamin protein, and that are functionally equivalent to the mouse striamin protein (e.g., the protein that was detected in Example 5, which is encoded by a human transcript 3.1 kb in length). When hybridizing DNA is isolated from other organisms, animals including, but not limited to, humans, rats, rabbits, and cattle are used for the isolation. For this purpose, tissues such as skeletal muscles, in particular, are suitable. DNAs thus isolated, which encode proteins functionally equivalent to the mouse striamin protein, generally show significant homology with the DNA encoding the mouse striamin protein (SEQ ID NO: ). The term "significant homology" indicates a sequence identity of at least 40%, preferably at least 60%, more preferably at least 80%, and most preferably at least 95% at amino acid level. The degree of homology can be determined according to the algorithm described in the literature (Wilbur, W. J. and Lipman, D. J. Proc. Natl. Acad. Sci. USA (1983), 80:726–730).

The "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. The programs are available at the web site of the National Center for Biotechnology Information.

Examples of conditions used for the hybridization are as follows. For "low stringency" hybridization, after prehybridization for at least 30 minutes at 55° C. using "ExpressHyb Hybridization Solution" (CLONTECH), hybridization is carried out by adding a labeled probe and incubating for at least one hour at 37 to 55° C., followed by washing the filter three times in 2×SSC containing 0.1% SDS for 20 minutes at room temperature and then once in 1×SSC containing 0.1% SDS for 20 minutes at 37° C. For "medium stringency" hybridization, after prehybridization for at least 30 minutes at 60° C. using "ExpressHyb Hybridization Solution" (CLONTECH), hybridization is carried out by adding a labeled probe and incubating for at least one hour at 60° C., followed by washing the filter three times in 2×SSC containing 0.1% SDS for 20 minutes at room temperature and then twice in 1×SSC containing 0.1% SDS for 20 minutes at 50° C. For "high stringency" hybridization, after prehybridization for at least 30 minutes at 68° C. using "ExpressHyb Hybridization Solution" (CLONTECH), hybridization is carried out by adding a labeled probe and incubating for at least one hour at 68° C., followed by washing the filter three times in 2×SSC containing 0.1% SDS for 20 minutes at room temperature and then twice in 0.1×SSC containing 0.1% SDS for 20 minutes at 50° C.

The present invention also relates to the DNA encoding the striamin protein of the present invention. The DNA of the present invention may be any DNA including genomic DNA and synthetic DNA as well as cDNA, as long as it encodes the aforementioned striamin protein. The DNA of the present invention can be used, for example, to produce recombinant proteins. Such recombinant proteins can be prepared by inserting the DNA of the present invention (e.g., SEQ ID NO:1) into an appropriate expression vector. This is then introduced into appropriate cells to obtain a transformant, followed by culturing the transformants, and by purifying the expressed protein. Cells used for the production of recombinant proteins include, but are not limited to, mammalian cells such as COS, CHO, and NIH3T3 cells, insect cells such as Sf9 cells, yeast cells, and E. coli cells. Although vectors used for expression of recombinant proteins in the cell will vary depending on the host cells, such vectors include, for example, pcDNA3 (Invitrogen) and pEF-BOS (Nucleic Acids Res. 1990, 18 (17), p. 5322) for expression in mammalian cells, "BAC-to-BAC baculovirus expression system" (GIBCO BRL) for expression in insect cells, "Pichia Expression Kit" (Invitrogen) for expression in yeast cells, and pGEX-5X-1 (Pharmacia) and "QIAexpress system" (Qiagen) for expression in E. coli cells. Introduction of the vector into the host cells can be carried out using methods including the calcium phosphate, DEAE dextran, cationic liposome DOTAP (Boehringer Mannheim), electroporation, and calcium chloride methods. The transformants can be cultured using a method well known to one skilled in the art, using an appropriate existing method, depending on the properties of the particular transformant. Recombinant proteins may be purified from the transformants thus obtained may be carried out using, for example, the method described in the literature "The Qiaexpressionist Handbook, Qiagen, Hilden, Germany."

The DNA of the present invention can be used in gene therapy for diseases caused by mutations that have occurred in the DNA. As used in gene therapy, the DNA of the present invention is inserted into a vector such as adenoviral (e.g., pAdexLcw) or retroviral (e.g., pZIPneo) vectors for in vivo administration. Administration can be carried out via either an ex vivo or in vivo process.

The present invention also features a DNA molecule that contains at least 15 nucleotides, and that can specifically hybridize with the DNA encoding the striamin protein of the present invention or the complementary DNA thereof. The term "specifically hybridize" indicates that no significant cross-hybridization occurs to DNA encoding other proteins under standard hybridization conditions, preferably under stringent hybridization conditions. Such DNA molecules include probes, primers and nucleotides, and nucleotide derivatives (e.g., antisense oligonucleotides ribozymes, etc.), that can specifically hybridize to the DNA encoding the protein of the present invention or to the complementary DNA thereof.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The present invention includes an antisense oligonucleotide hybridizing to any portion of the nucleotide sequence of, for example, SEQ ID NO:2. Preferably, such an oligonucleotide is antisense to a continuous 15 nucleotides or more in length in the nucleotide sequence of SEQ ID NO:2. More preferably, the aforementioned continuous sequence 15 nucleotides or more in length contains a translation initiation codon.

Derivatives or modified oligonucleotides can be used as an antisense oligonucleotide. Such modified nucleotides include lower alkylphosphonate-modified, such as methylphosphonate- or ethylphosphonate-modified, phosphorothioate-modified, and phosphoroamidate-modified nucleotides.

As used here, the term "antisense oligonucleotides" means not only an oligonucleotide complementary to all of the continuous nucleotides comprising the given region of DNA or mRNA, but also oligonucleotides having one or more nucleotides mismatched against the continuous nucleotides, as long as DNA or mRNA and the oligonucleotides are able to specifically hybridize to the nucleotide sequence of SEQ ID NO:2.

Such DNAs include continuous nucleotide sequences at least 15 nucleotides in length, showing at least 70%, preferably at least 80%, more preferably at least 90%, and most preferably at least 95% homology with the nucleotide sequence of SEQ ID NO:2. An algorithm that can be used to determine the extent of homology is given herein. These DNAs are useful as probes to detect or isolate the DNA encoding the protein of the present invention, according to the methods described below in the Examples. They are also useful primers for amplification.

The antisense oligonucleotide derivatives of the present invention act upon the cells producing the protein of the present invention. They bind to the DNA or mRNA encoding the protein, inhibiting the transcription or translation of the protein and promoting the degradation of the mRNA. As expression of the protein is inhibited, there is an inhibitory effect on the functioning of the protein.

The antisense oligonucleotide derivatives can be formulated into external preparations such as liniments and poultices by mixing with a suitable base material, which is inert to the derivatives.

If necessary, the derivatives can be formulated into tablets, powders, granules, capsules, liposome capsules, injections, solutions, nose-drops and into freeze-dried agents, by adding excipients, isotonic agents, dissolving auxiliaries, stabilizers, preservatives and pain-killers. These formulations can be prepared using a standard technique.

An antisense oligonucleotide derivative of the present invention could be given to a patient by direct application onto the affected site or by intravascular administration. A mounting medium for including antisense derivatives can also be used to increase sustainability and membrane-permeability of the formulations. For example, liposome, poly-L lysine, lipid, cholesterol and lipofectin or derivatives thereof can be used.

A range of dosages of the antisense oligonucleotide derivatives, from 0.1 to 100 mg/kg, can be administered, depending on the patients' conditions.

The antisense oligonucleotides, or an inhibitor containing an antisense oligonucleotide, inhibit the expression of the protein of the present invention, and are thus useful in inhibiting its biological activity.

The present invention also features a screening method for a compound that binds to the protein. The screening method comprises the following steps of:

(a) contacting a test sample with the protein of the present invention or a partial peptide thereof;

(b) detecting the binding activity of the test sample to the protein of the present invention or a partial peptide thereof; and (c) selecting a compound binding to the protein of the present invention or a partial peptide thereof.

The protein of the present invention used for screening may be recombinant or naturally occurring protein, or may be a partial peptide thereof. Any test sample can be used without particular restriction, including, for example, cell extracts, culture supernatants, products from fermented microorganisms, extracts from marine organisms, plant extracts, purified or crude proteins, peptides, nonpeptidic compounds, synthetic low molecular weight compounds and natural compounds.

A number of methods well-known to one skilled in the art can be used to screen for a protein binding to the protein of the present invention utilizing the protein of the present invention. One of these screening methods is immunoprecipitation. Typically, immunoprecipitation is conducted as follows. The gene encoding the protein of the present invention is inserted downstream of a promoter provided for expressing foreign genes, such as pSV2neo, pcDNA 1, and pCD8, to express the gene, for example, in mammalian cells. Any commonly available promoter may be used for the expression, including SV 40 early promoter (Rigby in Williamson (ed.), Genetic Engineering Vol.3, Academic Press, London, p. 83–141 (1982)), EF-1α promoter (Kim et al., Gene, 91:217–223 (1990)), CAG promoter (Niwa et al., Gene, 108:193–200 (1991)), RSV LTR promoter (Cullen, Methods in Enzymology, 152:684–704 (1987)), SR α promoter (Takebe et al., Mol. Cell. Biol. 8:466 (1988)), CMV immediate early promoter (Seed and Aruffo, Proc. Natl.

Acad. Sci. USA, 84: 3365–3369 (1987)), SV 40 late promoter (Gheysen and Fiers, J. Mol. Appl. Genet., 1:385–394 (1982)), and Adenovirus late promoter (Kaufman et al., Mol. Cell. Biol., 9:946 (1989), HSV TK promoter.

Any method for introducing and expressing a foreign gene in animal cells may be used to express the gene, including electroporation (Chu, G. et al., Nucl. Acid. Res. 15:1311–1326 (1987)), a calcium phosphate method (Chen, C. and Okayama, H. Mol. Cell. Biol. 7:2745–2752 (1987)), a DEAE dextran method (Lopata, M. A. et al., Nucl. Acid. Res. 12: 5707–5717 (1984); Sussman, D. J. and Milman, G., Mol. Cell. Biol., 4:1642–1643 (1985)), Lipofectin method (Derijard, B., Cell, 7:1025–1037 (1994); Lamb, B. T. et al., Nature Genetics, 5:22–30 (1993); Rabindran, S. K. et al., Science, 259:230–234 (1993)).

The protein of the present invention can be expressed as a fusion protein containing a monoclonal antibody recognition site, the specificity of which has been defined by introducing the monoclonal antibody recognition site (epitope) at the N or C terminus of the protein of the present invention. Epitope-antibody systems used for this purpose are commercially available (Jikken Igaku, Experimental Medicine, 13:85–90 (1995)). A number of vectors provided for expression of a gene as a fusion protein fused with β-galactosidase, a maltose binding protein, glutathione S-transferase, or a green fluorescent protein (GFP) via a multi-cloning site available from commercial sources.

To limit variation in characteristics between the protein of the present invention and its fusion protein, an epitope of restricted size is introduced to prepare the fusion protein. This can range from just below to just above ten amino acids. Such methods have been reported. A combination of an epitope, such as polyhistidine (His-tag), influenza hemagglutinin HA, human c-myc, FLAG, Vesicular stomatitis viral glycoprotein (VSV-GP), T7 gene 10 protein (T7-tag), human herpes simplex viral glycoprotein (HSV-tag) or E-tag (epitopes on monoclonal phages), and a monoclonal antibody that recognizes the epitope can be used as an epitope-antibody system to screen for a protein binding to the protein of the present invention (Jikken Igaku (1995), Experimental Medicine, 13:85–90).

In immunoprecipitation, an immunocomplex is formed when these antibodies are added to the cell lysate prepared using appropriate detergent. The immunocomplex comprises the protein of the present invention, a protein capable of binding to it, and the antibody. In addition to using the antibody against the epitope mentioned above, an antibody raised against the protein of the present invention can be used for the immunoprecipitation. Antibodies against the protein of the present invention can be prepared, for example, by introducing the gene encoding the protein of the present invention into an appropriate E. coli expression vector to express the protein in E. coli cells, purifying the expressed product, and immunizing animals, such as rabbits, mice, goats, and chickens, with the purified protein. Alternatively, the antibodies against the protein of the present invention can be prepared by immunizing the above animals with synthetic partial peptides of the protein of the present invention.

Immunocomplexes can be precipitated, for example, by using Protein A Sepharose or Protein G Sepharose, if the antibody is a mouse IgG antibody. When the protein of the present invention is prepared as fusion proteins fused with epitopes such as GST, substances specifically binding to the epitopes, such as glutathione-Sepharose 4B, can be used to form the immunocomplexes in the way that an antibody against the protein of the present invention is used.

A standard method of immunoprecipitation may be carried out as described in the literature; for example, Harlow, E and Lane, D: Antibodies, pp. 511–552, Cold Spring Harbor Laboratory publications, New York (1988).

SDS-PAGE is typically used to analyze the immunoprecipitated proteins. By using a gel with appropriate density, the bound proteins can be resolved by molecular size. In this procedure, the cells are cultured in a medium containing a radioisotope, such as 35S-methionine or 35S-cysteine, to label the proteins in the cells. The detection sensitivity is thereby increased, since, in general, proteins bound to the protein of the present invention are difficult to detect using conventional protein-staining methods such as Coomassie and silver staining. Once the molecular size of the protein is clarified, the protein of interest can be directly purified from SDS-polyacrylamide gel and subjected to sequencing.

West-Western blotting (Skolnik, E. Y. et al. Cell (1991), 65:83–90), for example, may be used to isolate proteins binding to the protein of the present invention by using the protein. In this method, the isolation is carried out by constructing a cDNA library from cells, tissue or an organ presumed to express binding proteins of the protein of the present invention (for example, myoblast cells and NIH3T3 cells) using a phage vector (e.g., λgt11, ZAP), expressing the vectors on LB-agarose, fixing the expressed proteins on the filter, reacting the filter with the labeled and purified protein of the present invention, and detecting the plaques expressing the proteins bound to the protein of the present invention through the label. The methods of labeling the protein of the present invention include those utilizing the affinity between biotin and avidin; those using an antibody binding specifically to the protein of the present invention, or a peptide or polypeptide fused to the protein of the present invention (for example, GST); those using a radioisotope; and those using fluorescence.

Another screening method of the present invention is to use the two-hybrid system using cells (Fields, S., and Sternglanz, R., Trends. Genet. (1994), 10:286–292). In two-hybrid systems methods, such as "MATCHMAKER Two-hybrid System," "Mammalian MATCHMAKER Two-hybrid Assay Kit," and "MATCHMAKER One-Hybrid System" (Clontech), or "HybriZAP Two-Hybrid Vector System" (Stratagene), and also as described in 'Characterization of SAP-1, a protein recruited by serum response factor to the c-fos serum response element' (Dalton S and Treisman R (1992), Cell 68:597–612), the protein of the present invention is fused to the SRF binding region or GAL4 binding region and expressed in yeast cells.

A cDNA library was prepared from cells predicted to express a protein that will bind to the protein of the present invention so as to express proteins fused to the VP16 or GAL4 transcriptional activation region. The cDNA library is then introduced into the above yeast cells, and the cDNA derived from the library is isolated from the positive clones detected (when a protein binding to the protein of the present invention is expressed in yeast cells, the binding of the two activates a reporter gene making positive clones detectable). The isolated cDNA can be introduced into E. coli to express a protein encoded by it. This method also allows preparation of a protein binding to the protein of the present invention and the gene encoding it. The reporter genes include Ade2, LacZ, CAT, and luciferase genes as well as HIS3 gene.

Affinity chromatography can be used to screen for the compound binding to the protein of the present invention. For instance, the protein of the present invention is immobilized on the support of the affinity column, to which a test sample is applied. The test sample is selected to express the protein that binds to the protein of the present invention; a cell extract or cell lysate can be used. After the test sample is applied, the column may be washed to prepare the protein bound to the protein of the present invention.

The amino acid sequence of the protein thus obtained may be analyzed and, based on the result, oligo-DNA is synthesized and used as a probe for screening the cDNA library to obtain the DNA encoding the protein.

The present invention may include use of a biosensor in which a surface plasmon resonance phenomenon is utilized to detect or determine the bound compounds. The biosensors utilizing a surface plasmon resonance phenomenon (e.g., BIAcore, Pharmacia) enable the real-time observation of the interaction between the protein of the present invention and the test compound as surface plasmon resonance signals, using a small amount of the protein without the need for labeling. Consequently, the binding of the protein of the present invention and the test compound can be estimated using a biosensor such as BIAcore.

Among methods for isolating compounds, not limited to proteins, that bind to the protein of the present invention, those methods of screening for molecules that bind to the protein of the present invention by making synthetic compounds, a natural substance bank, or a random phage peptide display library, act on the immobilized protein of the invention. Furthermore, methods of screening using a high-throughput based on combinatorial chemistry techniques are well known to one skilled in the art. (Wrighton N C; Farrell F X; Chang R; Kashyap A K; Barbone F P; Mulcahy L S; Johnson D L; Barrett R W; Jolliffe L K; Dower W J. 'Small peptides as potent mimetics of the protein hormone erythropoietin', Science (United States) Jul. 26, 1996 273:458–64, Verdine G L., 'The combinatorial chemistry of nature'. Nature (England) Nov. 7, 1996, 384:11–13, Hogan J C Jr., 'Directed combinatorial chemistry'. Nature (England) Nov. 7, 1996, 384:17–9).

The present invention also relates to a method for screening for a compound able to promote or inhibit the activity of the protein of the invention. Since the protein of the present invention has inhibitory activity on the differentiation of myoblasts into myotubes, a compound able to promote or inhibit activity of the protein of the invention can be screened by using this activity as an indicator. Such screening can be done using a method comprising the steps of:

(a) exposing the protein of the present invention to myoblast cells in the presence of a test sample, (b) detecting the differentiation of the cells into myotube cells, and (c) selecting a compound that increases or reduces the inhibitory effect of the protein of the present invention by comparing with the results of the assay performed in the absence of the test sample.

The protein of the present invention used for the screening can be a naturally occurring protein or a recombinant protein, or a purified protein or the supernatant of cell culture (when the protein is secreted from the cell).

There are no particular restrictions as to the test samples used. For example, cell extracts, culture supernatants, products from fermented microorganisms, extracts from marine organisms, plant extracts, purified or crude proteins, peptides, nonpeptidic compounds, synthetic low molecular weight compounds and natural compounds may be used. Alternatively, a compound obtained by the aforementioned screening for compounds binding to the protein of the present invention can be used as a test sample.

Myoblasts used for detecting the differentiation into myotube cells, preferably include, but are not limited to, C2C12 myoblasts. The differentiation into myotubes can be detected by a method, such as that for determining the differentiation potency of the C2C12 myoblast cell line into multinucleate myotube cells when they are cultured in the presence of both the test sample and the protein of the present invention, using the culture system of the mouse C2C12 myoblast line described in the Examples (the mouse myoblast cell line C2C12 differentiates into multinucleate myotube cells when cultured in the DMEM medium free of serum or containing 2% equine serum).

The protein of the present invention has here been shown to inhibit the transcriptional factor activity of p53. Therefore, a compound promoting or inhibiting the activity of the protein can also be screened conducted using the transcriptional factor activity as an indicator. This screening can be carried out by:

(a) providing p53-deficient cells in which vectors expressing the protein, p53 and a reporter gene responsive to p53 have been introduced, (b) exposing the test sample to the cells, (c) detecting the reporter activity in the cells, and (d) selecting a compound that increases or reduces the reporter activity compared with the activity detected in the absence of the test sample (control).

Specifically, a test sample is added to the detection system described in Examples 8 and 9, in which inhibition of the transcriptional factor activity of p53 by striamin is detected, reporter activity is detected, and then the compound altering the activity may be selected. There are no particular restrictions as to the test samples used. For example, cell extracts, culture supernatants, products from fermented microorganisms, extracts from marine organisms, plant extracts, purified or crude proteins, peptides, nonpeptidic compounds, synthetic low molecular weight compounds, and natural compounds may be used. Alternatively, a compound obtained by the aforementioned screening for compounds binding to the protein of the present invention can be used as a test sample.

The striamin expression vector may express striamin fully or it may express a partial peptide of striamin which can inhibit the transcriptional factor activity of p53 (e.g., C-terminus of striamin). Preferably, the chosen p53 vector should express p53 controllably. Such vectors include temperature-sensitive p53 expression vectors.

A plasmid expressing the reporter in response to p53 has the reporter gene located downstream of a p53 responsive sequence. "ATGCTTGCCC" (SEQ ID NO:17) may be used as the p53 responsive sequence. There are no particular restrictions as to the reporter gene used as long as it has a detectable response. Genes such as those for luciferase and β-galactosidase can be used.

Preferably, p53-deficient cells are used in vector introduction to avoid the expression of the reporter gene by the action of endogenous p53. Such cells include p53-/-murine fetal fibroblast cells.

If a reduction in reporter activity is detected during screening, compared with the activity found in the absence of the test sample (control), then the test sample used is determined as being a compound (or containing a compound) that promotes the activity of the protein of the present invention. Likewise, when the test sample increases the reporter activity, it is determined as being a compound (or containing a compound) that inhibits the activity of the protein of the present invention.

As used in the screening method, "a compound that promotes or inhibits the activity of the protein of the present invention" is any compound, without limit, promoting or inhibiting the signal transduction via the protein of the present invention. Specifically, such a compound is not limited to ones that promote or inhibit the activity by directly acting on the protein of the present invention. A compound that promotes or inhibits the signal transduction by action on any of the downstream factors from the protein of the present invention in the signal transduction is also included.

The compounds obtained from the screening of the present invention will be candidate agents that promote or inhibit the activity of the protein of the present invention, or that promote or inhibit the signal transduction via the protein of the present invention, for a disease associated with the protein of the present invention. The compounds obtained using the screening method of the present invention include any substance in which a portion of the structure of a compound having the binding activity to the protein of the present invention that is obtained using the screening method of the present invention and has been altered by addition, deletion and/or substitution.

To use the compounds obtained with the screening method of the present invention as drugs for humans and other mammals such as mice, rats, guinea pigs, rabbits, chickens, cats, dogs, sheep, pigs, cattle, monkeys, baboons, and chimpanzees, the compounds may be formulated for administration to the patients by a well-known pharmaceutical preparation method, as well as direct administration of the isolated compounds. For example, the drugs can be administered orally in the form of sugar-coated tablets, capsules, elixirs, or microcapsules, or parenterally in the form of injections of sterile solutions or suspensions with water or any other pharmaceutically acceptable liquid as needed. The compounds may be formulated by adequately combining them with pharmacologically acceptable carriers or media, specifically, sterilized water or physiological saline, vegetable oil, emulsifiers, suspensions, surfactants, stabilizers, flavoring agents, excipients, vehicles, preservatives and bonding agents, and mixing in a unit dose form required for generally accepted drug implementation. The amount of each effective ingredient in these preparations is provided for giving a suitable dosage acquirable within the indicated range.

Additives mixable in the tablets and capsules include a bonding agent such as gelatin, corn starch, tragacanth gum or arabic gum; an excipient such as crystalline cellulose; a swelling agent such as corn starch, gelatin or alginic acid; a lubricator such as magnesium stearate; a sweetener such as sucrose, lactose or saccharin; and a flavoring agent such as peppermint, Gaultheria adenothrix oil and cherry. When the unit dosage form is a capsule, a liquid carrier such as oil can also be included in the above ingredients. Sterile compositions for injections can be formulated following normal drug implementations using vehicles such as distilled water used for injections.

Aqueous solutions for injection include physiological saline, and isotonic liquids containing glucose or other adjuvants, such as D-sorbitol, D-mannose, D-mannitol, and sodium chloride. These solutions can be used in conjunction with suitable dissolution adjuvants, such as alcohol, specifically ethanol, polyalcohols such as propylene glycol and polyethylene glycol, and non-ionic surfactants such as poly sorbate 80 (TM) and HCO-50. Sesame oil or Soy-bean oil can be used as an oleaginous liquid and may be used in conjunction with benzyl benzoate or benzyl alcohol as dissolution adjuvants. They may also be formulated with a buffer, such as phosphate and sodium acetate buffer; a pain-killer, such as procaine hydrochloride; a stabilizer such as benzyl alcohol, phenol; and an anti-oxidant. The injection solution thus prepared is filled into a suitable ampoule.

Administration to the patients may be carried out using a method well known to one skilled in the art, for example, via intranasal, bronchial, intramuscular or oral route, as well as intra-arterial, intravenous or subcutaneous injection. While the doses vary depending on the patient's body weight and age and on the administration method, one skilled in the art may properly determine the adequate doses. If the compound can be encoded by DNA, gene therapy may possibly be carried out by incorporating the DNA into a vector for gene therapy. While the doses of the drug and the method for administration may vary depending on the patient's body weight, age and condition, one skilled in the art may determine them properly. The administered dose of a compound that binds to the protein of the present invention or promotes or inhibits the activity of the protein of the present invention will vary depending on the patient's condition. For oral administration, about 0.1 to about 100 mg per day, preferably about 1.0 to 50 mg per day, and more preferably about 1.0 to 20 mg per day may typically be administered to a normal adult (weighing 60 kg).

The parenteral dose to be administered varies depending on the subject for administration, target organ, subject's conditions, and the method of administration. In the form of an injection, for example, a dose of about 0.01 to about 30 mg per day, preferably about 0.1 to about 20 mg per day, and more preferably about 0.1 to about 10 mg per day may be advantageously administered to a normal adult (weighing 60 kg) by intravenous injection. For other animals, the dose calculated to body weight of 60 kg may be administered to the animal.

BRIEF DESCRIPTION OF THE DRAWINGS

FIG. 1 shows the nucleotide sequence of striamin and its predicted amino acid sequence (SEQ ID NOs:2 and 1, respectively). The sequence of in-frame codons and the 5' upstream sequence obtained by 5' RACE PCR on the mouse skeletal muscle cDNA are underlined.

FIG. 2(panel B) shows the Western blotting of the recombinant striamin protein obtained from *E. coli* transformed with IPTG-induced pQE30/striamin, using an anti-His antibody. The signal was detected at the position of approximately 18 kD (indicated by an arrow).

FIG. 4(panel B) shows the Northern analysis of RNA from the muscle fibers including fast-and slow-twitch fibers at various ratios.

Lane 1, quadriceps (95% fast-twitch fibers 2B, 4% fast-twitch fibers 2X);

Lane 2, extensor digitorum longus muscle (60% fast-twitch fibers 2B, 28% fast-twitch fibers 2X, 12% fast-twitch fibers 2A);

Lane 3, outer layer of the gastrocnemius muscle (100% fast-twitch fibers 2B);

Lane 4, diaphragm (57% fast-twitch fibers 2X, 34% fast-twitch fibers 2A, 7% slow-twitch fibers);

Lane 5, soleus muscle (45% fast-twitch fibers 2A, 55% slow-twitch fibers). Striamin is intensively expressed in the fast-twitch fibers 2B that have a glycolytic function. 18S ribosomal RNA was used as a control.

Figure 4:
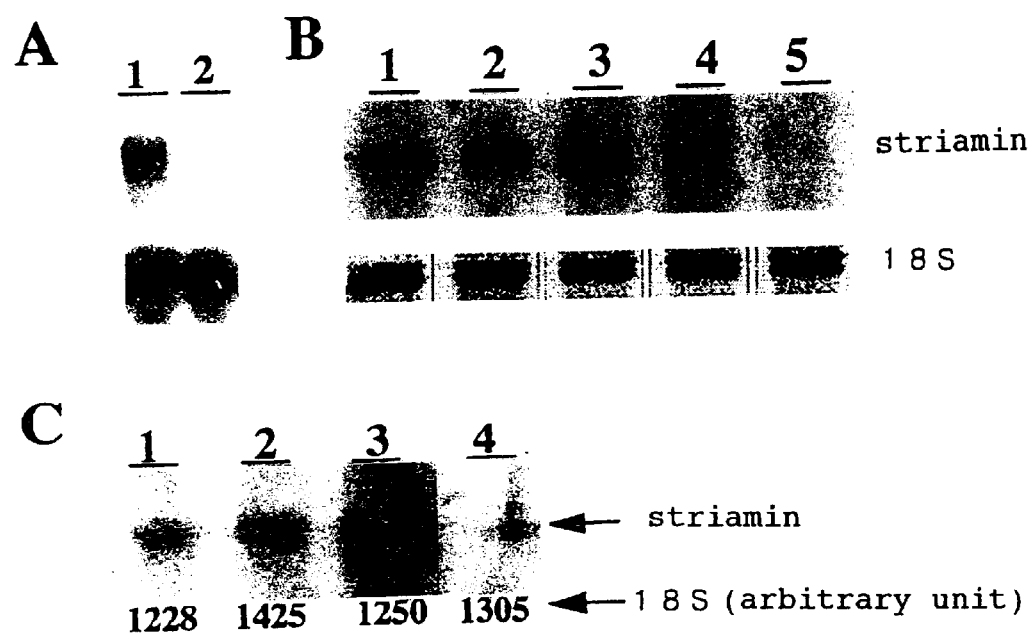
FIG. 4(panel A) shows detection of the striamin expression in different muscles by Northern analysis. The expression was detected in the fast-twitch fibers (quadriceps, Lane 1), but not in the slow-twitch fibers (soleus muscle, Lane 2).

FIG. 4(panel C) shows the striamin expression in the differentiating C2C12 cells in vitro.

Lane 1 RNA from the myoblasts differentiating in low-density culture.

Lane 2 RNA from the differentiating myoblasts in moderate-density cell culture.

Lane 3 RNA from C2C12 cells cultured for one day in the differentiation medium;

Lane 4 RNA from C2C12 cells cultured for four days in the differentiation medium and forming a large number of myotubes. 18S ribosomal RNA was used as a control.

FIG. 5 shows the effect of striamin on the in vitro differentiation of C2C12 cells. Myotube formation was not observed in the cells transformed with striamin and cultured for 72 hours in the differentiation medium (B), but was observed in the control (A).

Figure 6:
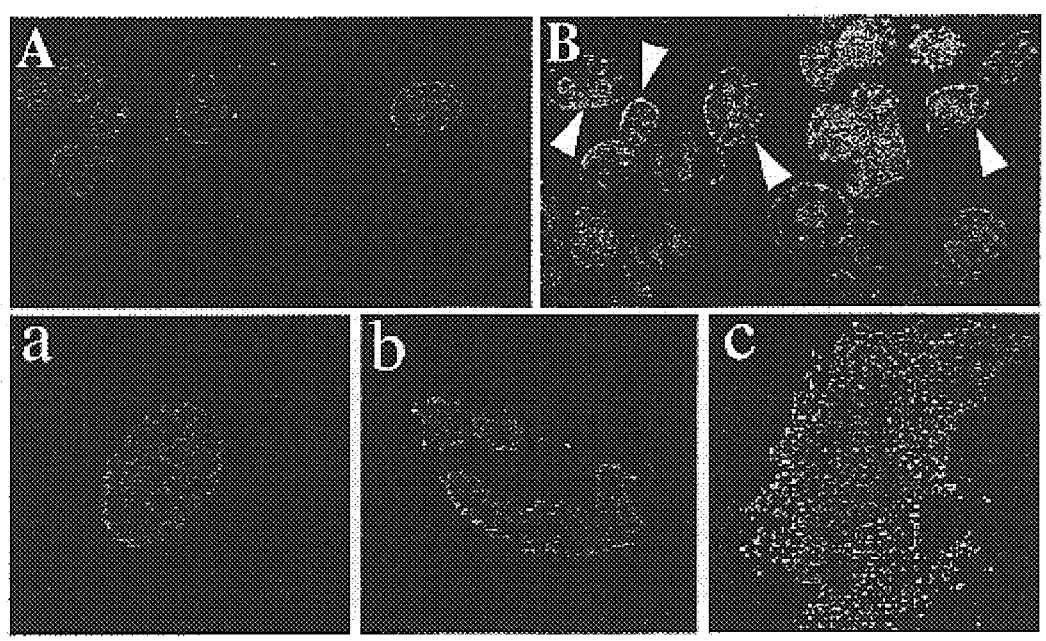

FIG. 6 depicts the intracellular localization of striamin. In COS7 cells transfected with pEGFPC1-striamin, green fluorescence from the GFP-striamin fusion protein was identified in the nuclei (A). The nuclei shown in A were stained with Hoechst dye (B) and indicated by arrow heads.

To show that their expressions are localized in the nucleus, perinuclear space, and cytoplasm, pEGFPC1-striamin (a), pEGFPC1-striamin N75 (b), and pEGFPC1-striamin C74 (c) were microinjected into NIH3T3 cells.

Figure 7:
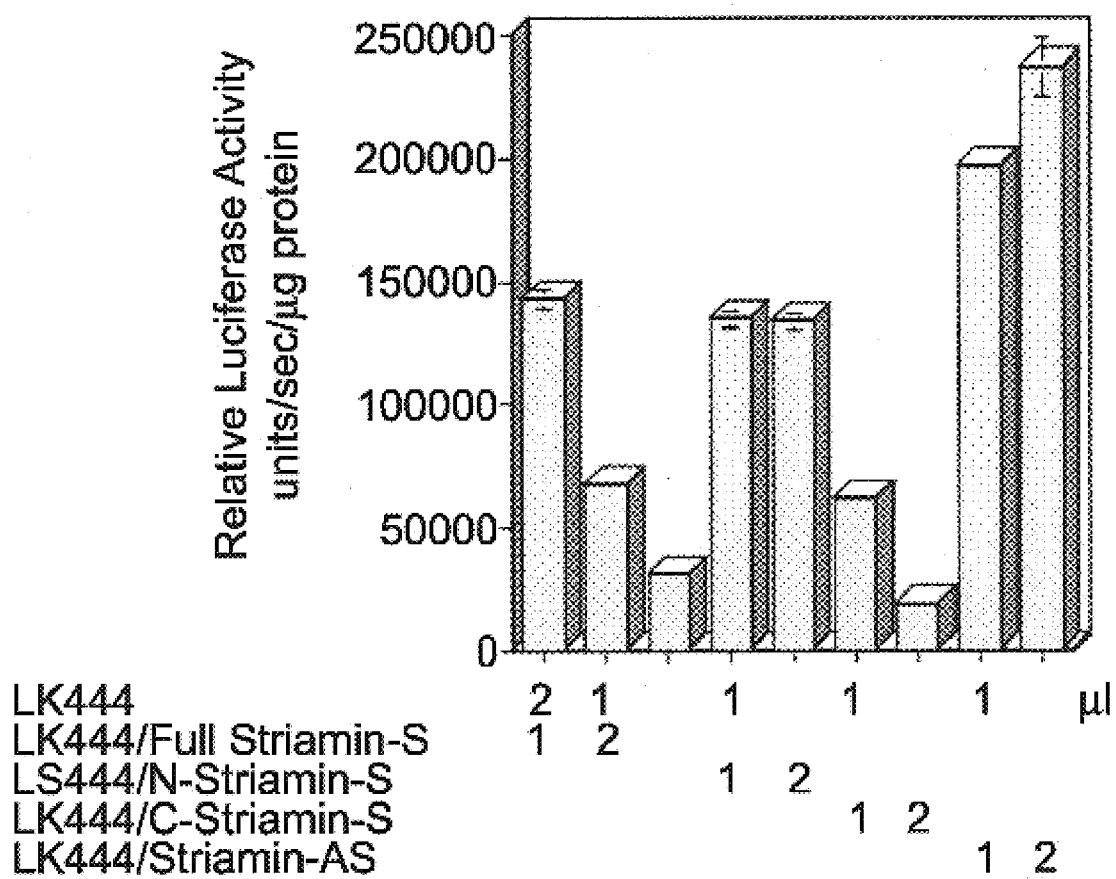

FIG. 7 shows the results of the detection of the interaction between striamin and p53 using luciferase as a reporter. The p53 expression plasmid, the p53-responsive luciferase expression plasmid, and the different striamin expression plasmids were introduced into p53-/-mouse embryonic fibroblast (MEF) cells, and the luciferase activity was detected. The amount of each plasmid (0.5 $\mu g/\mu l$) used is indicated by the figures "1" and "2". Error bars denote the standard deviations (n=3).

Figure 8:
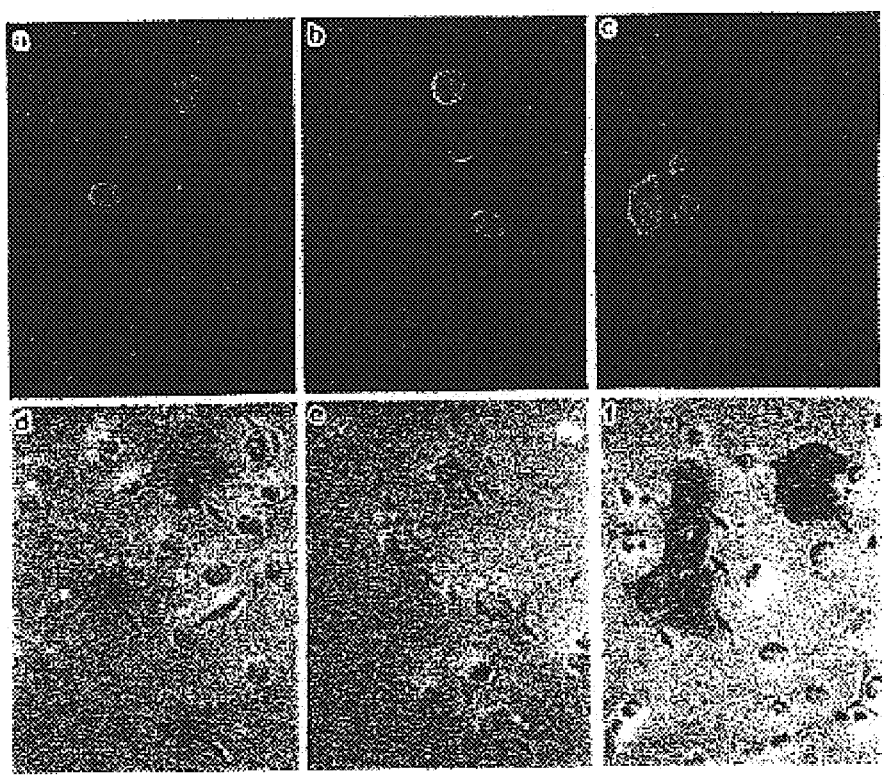

FIG. 8 shows the results of the detection of the interaction between striamin and p53 using β-galactosidase as a reporter. The p53 expression plasmid, the p53-responsive β-galactosidase expression plasmid, and the different striamin expression plasmids were introduced into p53-/-mouse embryo fibroblast (MEF) cells, and the β-galactosidase activity was detected (arrows in d, e, and f). In addition, to identify the cells injected with DNA, control IgG was microinjected together with the above plasmids into the cells to detect FITC conjugated anti-rabbit IgG (a, b, and c).

Figure 9:
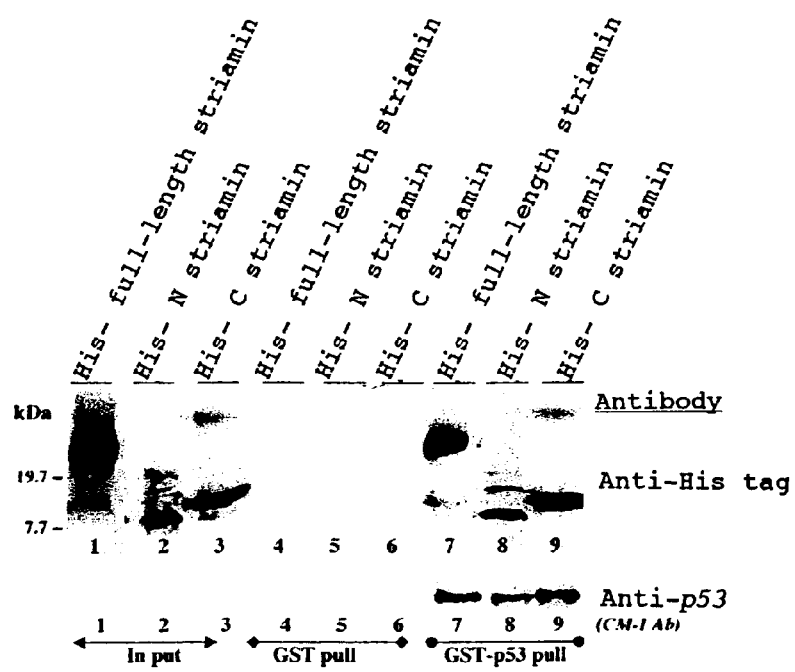

Control, a and d; sense-vectors: b and e; antisense-vectors: c and f. FIG. 9 shows the results of detecting the interaction between striamin and p53 in vitro. Different striamins conjugated to histidines were reacted with p53 conjugated to GST in vitro, and the reaction was immuno-precipitated with glutathione Sepharose beads, followed by Western blot analysis using anti-histidine-tag and anti-p53 antibodies ("GST-p53 pull" in the figure).

"In put" in the figure represents the results of Western blot analysis of the reaction made without adding GST. "GST-Pull" represents the results of the immunoprecipitation in which GST was added instead of GST-p53, followed by Western blot analysis. "GST-p53 Pull" represents the results of the immunoprecipitation in which GST-p53 was added, followed by Western blot analysis.

Figure 10:
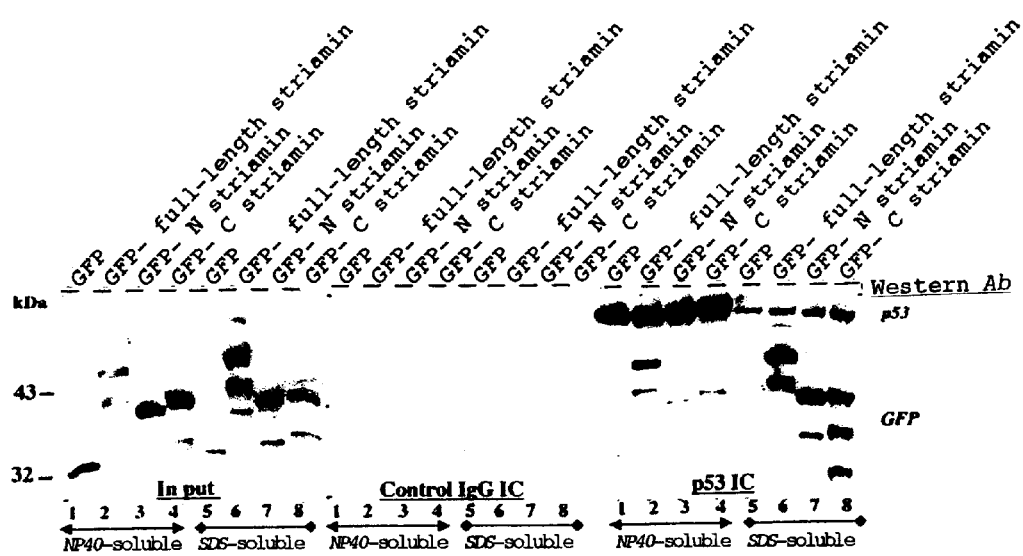

FIG. 10 shows the results of detecting the interaction between striamin and p53 in vivo.

The vectors expressing different striamins conjugated to GFP were introduced into COS7 cells, and the recombinant proteins were expressed in the cells and reacted with endogenous p53. Cell extracts from these cells were separated into two fractions, an NP-40 lysed fraction and an SDS lysed fractions. These fractions were immunoprecipitated by incubation with anti-p53 antibody, followed by addition of protein A/G-Sepharose. The immunocomplex thus obtained was subjected to SDS-PAGE, followed by Western blotting using anti-GFP and anti-p53 monoclonal antibodies ("p53IC" in the figure).

Immunoprecipitation was carried out using control IgG instead of anti-p53 antibody for the detection ("Control IgG IC" in the figure). Additionally, without carrying out the immunoprecipitation using anti-p53 antibody, SDS-PAGE was performed on the cell lysate (10% of the total amount of the protein used for the immunoprecipitation), followed by detection using anti-GFP monoclonal antibody ("In put" in the figure).

FIG. 11 shows the location of striamin on the mouse chromosome at the metaphase. Specific probes for striamin and chromosome 12 were made visible as green fluorescence at the positions indicated by arrows. Striamin was localized on the 12C3 region.

DETAILED DESCRIPTION OF THE INVENTION

The present invention will be explained in detail below with reference to examples, but is not to be construed as being limited thereto.

EXAMPLE 1

Cell Culture

Normal mouse embryonic fibroblast cells (CMEF) derived from mouse CD1-ICR cell line, an immortalized clone (RS-4) established from CMEF, and NIH 3T3 cells, all of which were used for the comparison of the research on proteins and cloning, were cultured according to the description in the reference (Wadhwa et al. (1991), Mutat. Res. 13.256:243–254). COS7 cells used for transient transformation were cultured in Dulbecco's modified Eagle's minimum essential medium supplemented with 10% fetal bovine serum.

EXAMPLE 2

Cloning and Sequencing of cDNA

Comparing the Triton X-100 soluble cell membrane fraction from the normal mouse cells (CMEF) with that from the immortalized cells (NIH 3T3) revealed that an approximately 33 kDa protein is present in NIH 3T3 cells but not in CMEF cells (Wadhwa et al. (1991), Mutat. Res. 13.256:243–254). This protein was separated from the SDS polyacrylamide gel and used to generate the polyclonal antibody. The anti-p33 antibody generated was used to clone cDNA via immunoscreening of the cDNA library derived from RS-4 cells and constructed with lambda ZAPII vectors. The resultant five clones obtained were characterized by partial sequencing using the T3 and T7 primers for pBluescript vectors. While three of the five clones were shown to be identical to the known genes, i.e., Fuschop (Rabbitts et al. (1993), Nat. Genet. 4:175–180; Kuroda et al. (1995), Am. J. Pathol. 147: 221–1227), G-utrophin (Blake et al. (1995), Proc. Natl. Acad. Sci. USA. 92:3697–3701) and dystrophin (Love et al. (1989), Nature 339:55–58), the remaining two clones did not have corresponding sequences in the nucleotide sequence database. The in vitro translated products of these two novel clones, however, were not precipitated with anti-p33 antibody. This fact shows that these two clones are not related to the 33 kDa protein derived from the immortalized cells and initially identified on SDS polyacrylamide gel. The inventors characterized clone #336, one of the clones isolated. The sequence of the cDNA clone was determined by the dideoxy chain termination method, and the reaction was analyzed by an ABI 377 automated sequencer.

The whole sequence of the cDNA named #336, which was 2.4 kb in length, was obtained by a method using 3'→5' exonuclease III (TAKARA Kilo Sequencing Deletion Kit, TAKARA Shuzo) and primer walking. The 5' terminal of the clone was obtained by means of 5' Marathon RACE polymerase chain reaction (PCR) on the mouse skeletal muscle cDNA, using three sequences of primer-specific antisense genes:

SP1 (SEQ ID NO:3: TGTCACTGCCACGCCTTCTC GGTGCGCAG),

SP2 (SEQ ID NO:4: TCCCGGCTGCCCTTTGGCCCA TCTTGTCCC), and

SP3 (SEQ ID NO:5: TGAGAAAGCGTTAGACGCTCT CAGAGCCCT).

5' Marathon RACE PCR was carried out according to the protocol in "Marathon-Ready™ cDNA Kit" (mouse skeletal muscle, catalogue #7456-1) (Clontech).

The complete sequence of the striamin cDNA thus obtained is shown in FIG. 1 and SEQ ID NO:1. No homologous sequence to this full-length cDNA was identified through the DNA databank search. The cDNA encodes a protein 149 amino acids in length (pI-10.2), and no counterpart having significant homology to this protein was identified in the protein database. No known motif that allows prediction of the function of the protein was identified by cDNA analysis using BLAST, PROSITE, GCG, and PSORT programs. The 5' untranslated region of striamin was found to have a "C/GAAAA" repeat, and the 3' untranslated region was found to have a "GT" repeat. ProtPram analysis predicted that the protein has characteristics of soluble proteins with a standard hydrophobicity of 0.5 and with aliphatic index of 0.74. Analysis by the ScanProsite program revealed the presence of two protein kinase C phosphorylation sites, i.e., "SDR" (one letter codes of amino acids) at the position of amino acid residues 45 to 47, and "SPK" (one letter codes of amino acids) at the position of amino acid residues 78 to 80; a casein kinase II phosphorylation site, i.e., "SGLD" (one letter codes of amino acids/SEQ ID NO:6) at the position of amino acid residues 12 to 15; and two myristylation sites, i.e., "GNYYCC" (one letter codes of amino acids/SEQ ID NO:7) at the position of amino acid residues 111 to 116 and "GTRWAK" (one letter codes of amino acids/SEQ ID NO:8) at the position of amino acid residues 120 to 125. Other interesting characteristics of this protein would be its highly positive net charge, and the presence of a large number of serine, leucine and proline residues, and four cysteines. Based on the sequence analysis of the cDNA and protein, striamin was not characterized as a member of any known gene family.

EXAMPLE 3

In vitro Transcription and Translation

The predicted ORF was cloned into pBSSK and subjected to in vitro translation to verify the presence of the ORF within the given sequence.

Specifically, the ORF was amplified from RS-4 cells by reverse transcription-polymerase chain reaction, using a sense primer (SEQ ID NO:9: GAARRCATGAAA GGCCTGGCTGGCGAG) and an antisense primer (SEQ ID NO:10: GAATTCTCATGTCACTGCCACGCCTTCTCG), and the amplified product was cloned into Bluescript vectors.

In vitro transcription (Transprobe T kit, Pharmacia) and translation of pBSSK/striamin were carried out for one hour in the rabbit reticulocyte lysate (Stratagene) containing L-[$^{35}$S]methionine. The translated products were separated on an SDS-polyacrylamide gel and visualized by autoradiography. In vitro translation products were also immunoprecipitated with anti-p33 antibody. As a result, an approximately 18 kDa protein was detected, and this agreed well with the protein predicted from the OFR within the sequence of #336 in the molecular weight (FIG. 1).

EXAMPLE 4

Preparation of Recombinant Striamin Proteins

Figure 2:
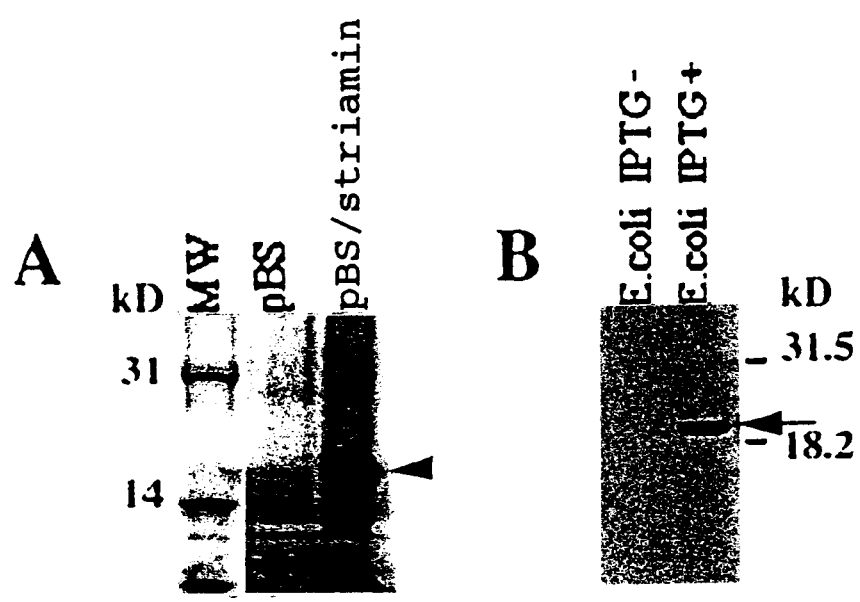
FIG. 2(panel A) shows the product from the in vitro translation system of plasmid pBS/striamin in which striamin ORF is placed downstream of the T3 promoter. This product is detected as a protein of 18 kD (indicated by an arrowhead) on SDS-PAGE.

The open reading frame of striamin cDNA was amplified from pBSSK/striamin by PCR using a sense primer containing a Bam HI site (SEQ ID NO:11: GGATCCAAGAAAGGCCTGGCTGGCGAG) and an antisense primer containing a Hind III site (SEQ ID NO:12: AAGCTTTCATGTCACTGCCACGCCTTC). The 0.5 kb fragment amplified by PCR was initially cloned into pGEM-T vector, and the integrity of the sequence was confirmed. The sequence was then excised with Bam HI and Hind III and finally cloned into pQE30 vector that produces a His-tagged protein (Qiagen). The pQE30/striamin construct was introduced into M15 bacterium. After growing to OD580=0.6, the cells were induced by isopropyl-b-thiogalactopyranoside (IPTG) (0.2 mM) for five hours at 37° C. The cell lysates of the bacterium (induced and non-induced by IPTG) were analyzed by SDS-PAGE, and subsequently by Western blotting using anti-His (Qiagen) and anti-p33 antibodies. The result revealed that an approximately 18 kDa protein was synthesized (FIG. 2). Similar to the result of the in vitro translation of the cDNA clone, the recombinant protein had the same size as was deduced from the sequence.

EXAMPLE 5

Northern Blot Analysis

Figure 3:
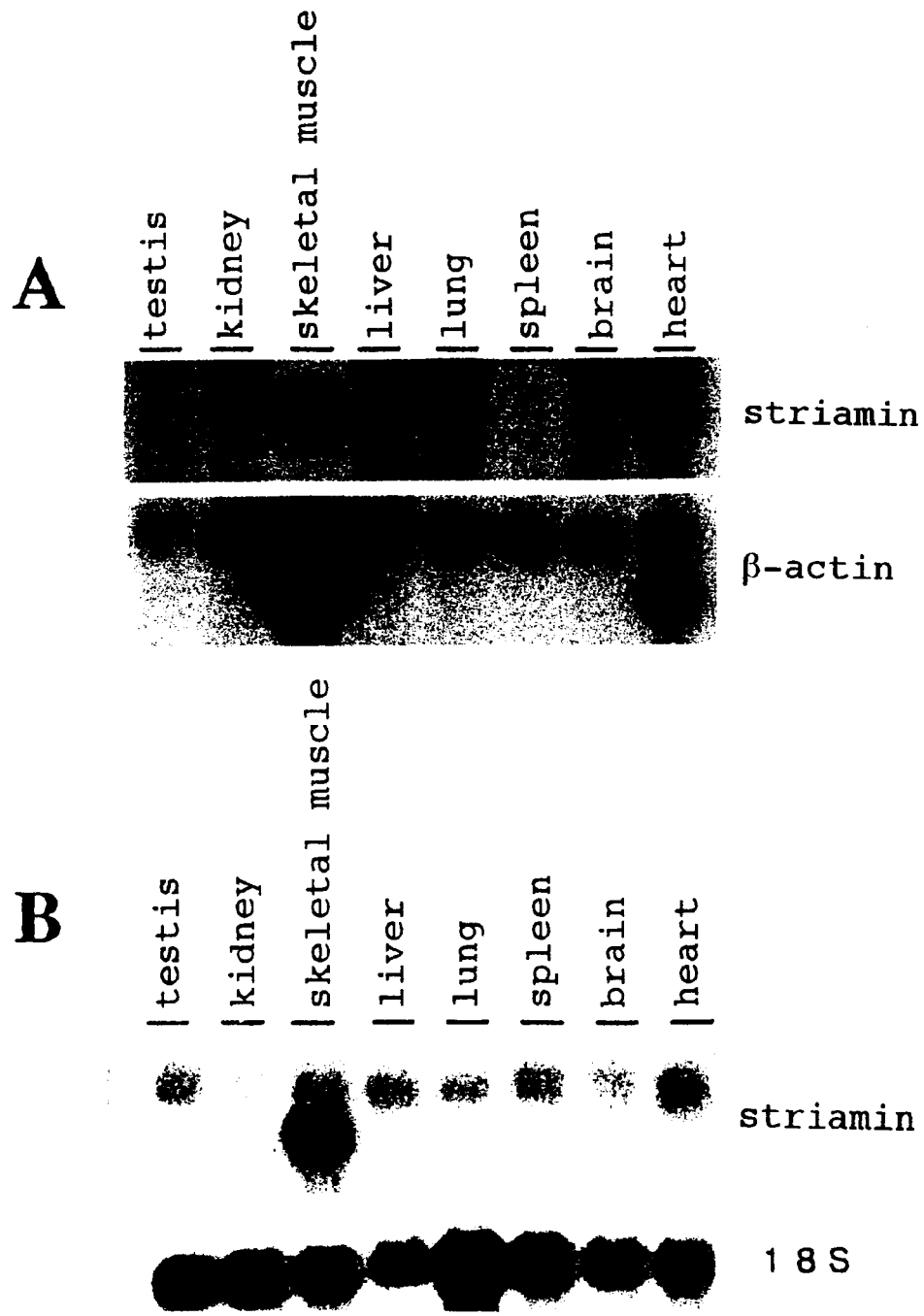
FIG. 3 shows the tissue specificity of the striamin expression in mice (A) and humans (B) analyzed by Northern blotting.

Northern blots, on which 2 μg/lane of poly (A+) RNA from a variety of tissues collected from humans and mice is blotted, were purchased from "Clontech Laboratories, Palo Alto, Calif." Northern blot analysis was carried out using 15 μg of total RNA prepared from each cell line. As a probe, the 1.4 kb fragment of the 3' untranslated region (UTR), which was recovered from the digestion with Bam HI of the plasmid #336, was used. Hybridization was carried out in the SSC-Denhardt's-SDS buffer at a temperature of 65° C. After being washed twice in 2×SSC, 2×SSC containing 0.1% SDS, 1×SSC, and then 1×SSC containing 0.1% SDS for 10 minutes each, the membrane was subjected to autoradiography to visualize the result. The amounts of RNA loaded on the blot were determined by hybridization using β-actin or 18S ribosomal RNA as a probe. From the Northern blot analysis of the expression of striamin in various tissues from a number of mice and humans, intensive reactivity against a single transcript of 3.0 kb from skeletal muscles of mice and humans was demonstrated (FIGS. 3A and B). A transcript of the same size was also shown to be expressed in the hearts of mice (FIG. 3A). Subsequently, the inventors examined whether this transcript is muscle fiber-type specific. The four phenotypes of the fibers, i.e., fast-twitch fibers 2A, 2B, and 2X, and type I slow-twitch fibers, are defined according to expression of isoforms of myosin heavy chains (Pette and Staron (1990), Rev. Physiol. Biochem. Pharmacol. 116:1–76). Striamin expression was more marked in the fast muscle (quadriceps muscle of thigh) than in the slow muscle (soleus muscle) (FIG. 4A). Northern blot analysis of mouse skeletal muscles in which contents of fast and slow fibers are varied, including quadriceps muscle of thigh (95% fast-twitch fibers 2B, 4% fast-twitch fibers 2X; Hamalainen and Pette (1993), J. Histochem. Cytochem. 41:733–743), extensor digitorum longus muscle (60% fast-twitch fibers 2B, 28% fast-twitch fibers 2X, 12% fast-twitch fibers 2A; Leferovich et al. (1995), J. Neuroscience 15:596–603), outer layer of the gastrocnemius muscle (100% fast-twitch fibers 2B; Zardnnn and Parry (1994), Muscle & Nerve 17:1308–1316), diaphragm (57% fast-twitch fibers 2X, 34% fast-twitch fibers 2A, 7% slow-twitch fibers; Zardnnn and Parry (1994), Muscle & Nerve 17:1308–1316), and soleus muscle (45% fast-twitch fibers 2A, 55% slow-twitch fibers; Lewis et al. (1982), J. Physiol. 325:393–401), demonstrated that striamin is predominantly expressed in the fiber 2B that has a fast glycolytic function (FIG. 4B).

The inventors then analyzed striamin expression during the myogenesis of C2C12 myoblast cells in vitro. The striamin expression of the cells cultured in differentiation medium for four days was negligible, compared to the culture in non-differentiation medium and one day culture in the differentiation medium (FIG. 4C).

EXAMPLE 6

Expression Cloning and Biological Activity

The striamin ORF was amplified by PCR using a sense primer having a Hind III site (SEQ ID NO:13: GGTAAGCTTATATTGTTTGCAACTACCT), and an antisense primer having a Bam HI site (SEQ ID NO:14: GGATCCCATGTGACCTAATGTTTCATGTCA). The fragment thus amplified was initially cloned into pGEM-T vector, and the integrity of the sequence was confirmed. The insert was digested with Bam HI and Hind III, and then incorporated into a mammalian expression vector LK444. This vector has a β-actin promoter for constitutive expression and a neo marker, and is essentially expressed in the mammalian cells cultured in the growth medium containing G418 for selection (Gunning et al. (1987), Proc. Natl. Acad. Sci. U.S.A. 84:4831–4835). Mouse C1C12 myoblast cell line was transformed using Lipofectamine (GIBCO-BRL), and the transformants were selected in the medium containing G418 (700 μg/ml). Differentiation of the G418-resistant clones into myotubes in vitro was analyzed in a medium containing 2% equine serum.

As a result, the cells transformed with the vector were observed to differentiate in the differentiation medium and develop myotubes. However, among eight clones transformed with selected #336, seven clones were not observed to develop myotubes to the same extent (FIG. 5). This result revealed that overexpression of #336 inhibited the differentiation of C2C12 cells in vitro.

EXAMPLE 7

Intracellular Localization of Striamin

The striamin ORF was inserted into the C-terminal of GFP ORF in pEGFPC1 vector (Clontech) in frame. This plasmid, which encodes the GFP-striamin fusion protein, was introduced into COS7 cells proliferating on the cover glass by Lipofectamine™ (Gibco BRL). The cover glass was fixed with a nuclear staining agent, Hoechst 33258 (Sigma) (5 to 10 μg/ml in the culture medium for 10 minutes prior to the cell fixation), and methanol/acetone (1:1). After washing with PBS three times, Fluoromount (Difco) was mounted on the cover glass. The cells were observed through an epifluorescence optic system Olympus BH-2 microscope, or a Zeiss Axiophot microscope coupled with a Cellscan System (Scanalytics, USA). As a result, the transformed cells exhibited distinct green fluorescence, overlapping with the Hoechst 33258 nuclear staining in the same cells (FIG. 6A).

Microinjections of pGFPC1/striamin, pGFPC1/N-terminal 75 amino acid residues of striamin, and pGFPC1/C-terminal 75 amino acid residues of striamin were performed directly into the nuclei of NIH3T3 cells grown on the cover glass, using an Eppendorf microinjector and a Nikon inverted microscope. As described above, the cells were fixed and then analyzed for nuclear localization of striamin. As a result, distinct green fluorescence in the nucleus was detected for pEGFPC1-striamin, while it remains in the cytoplasm for both striamin-N75 and striamin-C74 (FIG. 6B). As anticipated from amino acid composition of striamin, the data and the fact that striamin does not contain any known nuclear localization signal suggest that the conformation of the intact protein charged highly positively in the native form may be responsible for nuclear localization.

EXAMPLE 8

Analysis of the Effect of Striamin on p53 Activity (Luciferase Analysis)

Wild-type p53 has been demonstrated to function during the cell differentiation (Aloni-Grinstein et al. (1995), EMBO J. 14:1392–1401). The evidence to support this finding includes the facts that:

i) Over-expression of exogenous p53 or irradiation of cells can partially recover the tumor cell differentiation (Halevy et al. (1995), Science 267:1018–1021), ii) p53 mRNA is positively regulated during C2 differentiation, and iii) inhibition of endogenous wild-type p53 suppresses the hematopoiesis and cell differentiation of muscles (Soddu et al. (1996), J. Cell Biol. 134:193–204).

The role of p53 in the C2 differentiation is shown to be independent of its activity exerted during the cell cycle (Soddu et al. (1996), J. Cell Biol. 134:193–204). From this report's point of view, as well as considering the characteristics of striamin that localized in the nucleus and suppressed myogenic differentiation, the inventors suspected that striamin also has a certain effect on p53 activity. The inventors thus examined whether striamin could inhibit p53 activity. For this examination the experiments were independently quadruplicated.

A temperature-sensitive p53 expression plasmid (pMSVp53Val135) and p53-responsive luciferase reporter (PG-13luc) plasmid, and one of the different striamin expression vectors (a plasmid expressing LK444/full-length striamin-S, 75 amino acid residues at the N-terminal (LK444/N-striamin-S), or 74 amino acid residues at the C-terminal (LK444/C-striamin-S)), a plasmid expressing antisense RNA against the full-length striamin cDNA (LK444/strimain-AS), or a control plasmid (LK444 vector (Gunning et al. (1987), Proc. Natl. Acad. Sci. U.S.A. 84:4831–4835) were introduced into p53-/-mouse embryonic fibroblast (MEF) cells.

As shown in FIG. 7, the full-length striamin (sense-strand) reduced the p53 activity 4.6-fold, compared with the control. In contrast, antisense striamin increased the p53 activity 1.6 fold, compared with the control. An inhibitory effect of C-striamin was equivalent to that of the full-length striamin. However, the inhibitory effect on p53 activity was not detected for N-striamin. These results reveal that striamin can reduce the p53 transcriptional factor activity.

EXAMPLE 9

Analysis of the Effect of Striamin on p53 Activity (β-galactosidase Analysis)

p53-/-mouse embryonic fibroblast cells were microinjected with 0.1 μg/μl of each pMSVp53Val135, and p53 responsive β-gal reporter pRGC fos-lacZ (Oncogene, 1998, 16: 3317–3322), and LK444 (control), LK444/full-length striamin, or LK444/striamin-AS. To identify the cells successfully injected with DNA, a control IgG was also microinjected into the cells in conjunction with the plasmids above. After overnight culture at 32.5° C., the cells were fixed with 4% formaldehyde and treated with PBS containing 0.1% Triton X-100 on ice for five minutes to make the cells permeable to macromolecules, followed by washing three times with PBS.

Subsequently, the cells were stained with FITC-conjugated anti-rabbit IgG (the upper panels) in order to specify the cells into which the DNA was introduced. The stained cells are indicated by the arrows in the lower panels.

Detection of the effect of striamin on p53 activity (β-galactosidase expression) was conducted using a β-galactosidase staining kit (Boehringer Mannheim). The cells were observed by microscopy (Proris (AX70), Olympus). Blue cells were determined as positive for β-gal expression.

As a result, the cells into which a control plasmid (LK444) and an antisense striamin plasmid (LK444/striamin-AS) were introduced yielded 86% and 88% β-gal positive cells, respectively.

In contrast, only 5% of the cells into which the striamin sense plasmid (LK444/full-length striamin) was introduced were detected as positive (FIG. 8). Consequently, this study also supports that striamin inhibits p53 activity. This is consistent with the fact that striamin expression is accompanied by a reduction of C2C12 cell differentiation.

EXAMPLE 10

Interaction Between Striamin and p53 in vitro

That striamin has an effect on the function of p53 to activate transcriptions suggests the possibility of interaction between the two proteins. To study if striamin interacts with p53 in vitro, immunoprecipitation, followed by Western blotting, was carried out.
(1) Preparation of Different Striamins With a Histidine tag Attached (Fusion Proteins)

The DNAs encoding the full-length striamin, and N-terminal (75 amino acid residues) and C-terminal (74 amino acid residues) regions of striamin were inserted into an expression vector pQE30 (Qiagen) of E. coli to generate pQE30/full-length striamin, pQE30/N-striamin, and pQE30/C-striamin. These plasmids were introduced into E. coli, and the recombinant proteins were expressed and then purified.

Specifically, the cells were first centrifuged, and their pellet was suspended in Buffer A (10 mM Tris-Cl (pH 7.5), 150 mM NaCl, 20 mM imidazole, 6 M urea, and 5 mM β-mercaptoethanol) and was sonicated on ice for two minutes, followed by agitation for 30 minutes at room temperature. The extract was subjected to centrifugation at 15,000 g for 20 minutes. The supernatant was applied to the nickel-NTA-agarose affinity resin (0.5 ml) (Qiagen) and mixed for two hours at room temperature. The mixture was charged into the column, which was subsequently washed with 20 ml of TBS (10 mM Tris-Cl (pH 7.5) and 0.5 M NaCl (TBS)). The proteins adsorbed into the affinity resin were eluted with TBS solution containing 0.5 M imidazole, and the imidazole was removed using a PD-10 column (Pharmacia). The different striamins thus obtained were stored at −20° C. until use. The purity of the purified products was identified by SDS-PAGE and Western blot analysis using anti-His antibody.
(2) Analysis of Binding Between Different Striamins and p53

Each protein purified in step (1) (2 to 5 μg) was mixed with GST or GST-p53 (1 μg, Santa Cruz) in NP40-lysis buffer (500 μl). After two hours, glutathione-Sepharose beads (20 μl) were added to the suspension and rotated for mixing for one hour at 4° C. The beads were precipitated by centrifugation, washed three times with TBS and then boiled in SDS-sample buffer. Subsequently, SDS-PAGE was carried out for each sample, followed by detection of the respective striamins conjugated to the histidines by Western blotting using an anti-histidine-tag antibody. In addition, p53 was detected by Western blotting using anti-p53 antibody.

As a result, the respective striamins conjugated to histidines were shown to precipitate in the GST-p53 precipitation using glutathione-Sepharose beads (FIG. 9, Lanes 7 to 9). In conclusion, the full-length striamin, N-striamin, and C-striamin all interacted with p53.

In addition, to confirm the striamin expression in all the samples, samples without addition of GST were subjected to Western blot analysis as controls (Lanes 1 to 3). Striamin was shown to be expressed in each sample.

To verify that the striamins are not directly bound to GST, similar detection was conducted adding GST instead of GST-p53 (Lanes 4 to 6). The respective striamins were not bound to GST directly.

EXAMPLE 11

Interaction Between Striamin and p53 in vivo

COS7 cells with high transfection efficiency (expressing endogenous p53) were transfected with expression plasmids for the fusion proteins of GFP and either of the striamins (PEGFPC1/full-length striamin, pEGFPC1/N-striamin, or pEGFPC1/C-striamin), or the control (PEGFPC1 vector). The cell extracts were prepared after 48 hours. A soluble protein fraction in NP-40 cell lysis buffer was obtained in the preparation of the cell extracts. From the insoluble fraction in the NP-40 cell lysis buffer, a soluble fraction was obtained after addition of 0.5% SDS to this fraction and boiling it.

To each of these fractions, anti-p53 antibody (CM-1, Novocastra Laboratories Ltd.) was added. After incubating overnight at 4° C., protein A/G-Sepharose was added to the mixtures and allowed to react for 30 minutes at 4° C., followed by immunoprecipitation (centrifugation; 5000 rpm for 1 min.).

The immunocomplexes thus obtained were subjected to SDS-PAGE and then Western blotting using an anti-GFP monoclonal antibody (#8362-1, Clontech). Western blotting using anti-p53 monoclonal antibody (Ab-1, Calbiochem) was also carried out to detect the presence of p53.

The result revealed that the precipitation of endogenous p53 using anti-p53 polyclonal antibody (CH-1, Novocastra Laboratories Ltd.) coprecipitated the respective striamins bound to GFP (the right side lanes in FIG. 10). In particular, striamins were detected in the SDS soluble fractions (the right side lanes in FIG. 10, Lanes 6 to 8). This showed that striamin interacts with p53 intracellularly in COS cells. The endogenous p53 failed to bind to GFP (the right side lanes in FIG. 10, Lane 5).

In contrast, the striamins were not detected with immunoprecipitation using control IgG, instead of anti-p53 antibody, followed by Western blotting using anti-GFP monoclonal antibody (the central lanes in FIG. 10). However, GFP and GFP-bound striamin bands were detected as a result of SDS-PAGE of the cell lysate (10% volume of the protein used for immunoprecipitation), without undergoing immunoprecipitation using anti-p53 antibody, followed by Western blotting using anti-GFP monoclonal antibody (the left side lanes in FIG. 10).

EXAMPLE 12

Location on the Chromosome

Mouse P1 genomic clones were obtained via PCR screening of the P1 bacteriophage mouse genomic library, using #336 specific primers, i.e., a sense primer (SEQ ID NO:15: TGGTATTCTTATATTGTTTGCAACTAACTA) and an antisense primer (SEQ ID NO:16: GGAAGGCCATGTGACCTAATGTTTCATGTCA). P1 clones isolated were tested for hybridization with the 3' UTR region of the gene, subsequently used for determining their location on the chromosome by fluorescence in situ hybridization (FISH). DNA from a mouse P1 clone was labeled with digoxigenin-dUTP by nick-translation. After binding to mouse DNA cleaved in pieces, the labeled probe was hybridized to the metaphase chromosome derived from mouse embryonic fibroblast cells in solution containing 50% formamide, 10% dextran sulfate, and 2×SSC. After hybridization, the slide glass was incubated with fluorescence labeled anti-digoxigenin antibody, and the specific hybridization signal was detected by counter-staining with 4',6'-diamidino-2-phenylindole (DAPI). As a result, the medium-sized chromosome, which was considered to be chromosome 12 based on DAPI staining, was specifically labeled. In the second experiment, a specific probe for a centromere region of chromosome 12 was hybridized with the P1 clone. Striamin P1 was located on chromosome 12 (FIG. 8). A total of 80 metaphase cells were analyzed and 71 of these cells were specifically labeled. In particular, the measurements of the 10 cells that hybridized with chromosome 12 have revealed that striamin located on the 57% distal position from the boundary between heterochromatin and euchromatin toward the telomere region of chromosome 12, namely, toward the region associated with the band 12C3 (corresponding to human chromosome 14q21–22).

INDUSTRIAL APPLICABILITY

The present invention provides striamin protein that inhibits differentiation of myoblasts into myotubes, and the gene encoding striamin. As the striamin protein and gene of the present invention are thought to play a role in maintaining the cultured cells in an undifferentiated state, they are expected to be applied to, for example, cancer therapy. For the mouse and human genes, intense expression is found in heart and skeletal muscle at the tissue level, and applications to diseases associated with heart or muscle are contemplated. Moreover, the mouse and human genes are specifically expressed in the fast-twitch fibers of muscle fibers. Since the mechanism involved in the phenotypes of slow and fast muscle fibers still remains an unsolved question, analysis of the gene of the present invention is expected to show applicability to movement.

What is claimed is:

1. A substantially pure polypeptide comprising the sequence of SEQ ID NO:1.

2. A substantially pure polypeptide consisting of the amino acid sequence of SEQ ID NO:1.

3. A substantially pure polypeptide comprising the amino acid sequence of residues 76 through 149 of SEQ ID NO:1.

4. A substantially pure polypeptide consisting of the amino acid sequence of residues 76 through 149 of SEQ ID NO:1.

5. A substantially pure polypeptide comprising the amino acid sequence of residues 1 through 75 of SEQ ID NO:1.

6. A substantially pure polypeptide consisting of the amino acid sequence of residues 1 through 75 of SEQ ID NO:1.

* * * * *

SEQUENCE LISTING

<160> NUMBER OF SEQ ID NOS: 17

<210> SEQ ID NO 1
<211> LENGTH: 149
<212> TYPE: PRT
<213> ORGANISM: Mus musculus

<400> SEQUENCE: 1

Met Lys Gly Leu Ala Gly Glu Trp His Gln Asp Ser Gly Leu Asp Ile
 1               5                  10                  15

Arg Glu Lys Ala Glu Asp Phe Ser Leu Pro Trp Leu Leu Pro Arg Leu
            20                  25                  30

Met Ala Leu Val Met Gln Glu Glu Gly Arg Phe Arg Ser Asp Arg Asn
        35                  40                  45

His Gly Tyr Leu Arg Glu Trp Leu Arg Ile Gln Ala Leu Thr Ala Cys
    50                  55                  60

Leu Pro Ser Pro Leu Gly Arg Val His Tyr Ala Gln Cys Ser Pro Lys
65                  70                  75                  80

Gln Lys Gly Arg Leu Pro Arg Gly Trp Ala Ser Leu Pro Ser Leu Ser
                85                  90                  95

Val Leu Val Arg Ala Leu Arg Ala Ser Asn Ala Phe Ser Leu Gly Asn

```
                 100                    105                    110
Tyr Tyr Cys Cys Pro Trp Arg Gly Thr Arg Trp Ala Lys Gly Gln Pro
            115                    120                    125
Gly Glu Trp Ala Arg Pro Arg Ala Ser Ser Pro Ser Ala His Arg Glu
        130                    135                    140
Gly Val Ala Val Thr
145

<210> SEQ ID NO 2
<211> LENGTH: 2679
<212> TYPE: DNA
<213> ORGANISM: Mus musculus
<220> FEATURE:
<221> NAME/KEY: CDS
<222> LOCATION: (294)...(740)

<400> SEQUENCE: 2
gcaggtctga gttcaaggac agcctggtct acgcattgag ttctagaaca gccaaggcta       60
cacaaagaat ccctgtctta aaaacaaaa caaataaaa aacaaacaaa caaaaaacaa       120
aacaaaacaa aaacaacaaa aagaccaatg ggggaaaaaa gaaagaaaaa acaagaaaag      180
aaaaaagaat agcttccctg ttctctgcag ggtagtttta gtaatgaatg ctcaaagctc      240
cacagtctat ggcacccaag tggtattctt atattgtttg caactaacta tcc atg         296
                                                              Met
                                                                1 aaa ggc ctg gct ggc gag tgg cat cag gac tct ggc cta gac atc agg       344
Lys Gly Leu Ala Gly Glu Trp His Gln Asp Ser Gly Leu Asp Ile Arg
        5                   10                  15 gag aag gca gaa gac ttc tcc ctg ccc tgg ctg ctg cct aga ttg atg       392
Glu Lys Ala Glu Asp Phe Ser Leu Pro Trp Leu Leu Pro Arg Leu Met
            20                  25                  30 gcc tta gtc atg cag gaa gaa gga agg ttc aga agt gac agg aat cat       440
Ala Leu Val Met Gln Glu Glu Gly Arg Phe Arg Ser Asp Arg Asn His
        35                  40                  45 ggg tat tta agg gaa tgg ctt agg att cag gca ctg aca gct tgt ctg       488
Gly Tyr Leu Arg Glu Trp Leu Arg Ile Gln Ala Leu Thr Ala Cys Leu
50                  55                  60                  65 cct tcc cct ctg ggg agg gtc cac tat gcc cag tgt tca ccg aaa caa       536
Pro Ser Pro Leu Gly Arg Val His Tyr Ala Gln Cys Ser Pro Lys Gln
                70                  75                  80 aaa gga agg ctg cca aga ggc tgg gct tct ctg cca tcc cta agt gtg       584
Lys Gly Arg Leu Pro Arg Gly Trp Ala Ser Leu Pro Ser Leu Ser Val
            85                  90                  95 ctt gtc agg gct ctg aga gcg tct aac gct ttc tca ctc ggg aac tac       632
Leu Val Arg Ala Leu Arg Ala Ser Asn Ala Phe Ser Leu Gly Asn Tyr
        100                 105                 110 tac tgc tgt ccg tgg agg ggg aca aga tgg gcc aaa ggg cag ccg gga       680
Tyr Cys Cys Pro Trp Arg Gly Thr Arg Trp Ala Lys Gly Gln Pro Gly
115                 120                 125 gag tgg gca agg cca agg gcg agc tca cct tct gcg cac cga gaa ggc       728
Glu Trp Ala Arg Pro Arg Ala Ser Ser Pro Ser Ala His Arg Glu Gly
130                 135                 140                 145 gtg gca gtg aca tgaaacatta ggtcacatgg ccttcccctc cggccttagc           780
Val Ala Val Thr gtgcctacac atctgcacag agaaggagaa gaggttgagg agagaataga gcagtacaga      840
gccaactcaa acagcagcag cagacagaga gcacgagaca gaaggtgagg gcgcaggagg      900
agaggagcgg gccagaaggg acagtgagca gacagggaaa tgagcaaggg aggcagggggt    960
```

-continued

```
gggggcagaa cctcccatca tgcacttccg acaggtcact cagaggtcac gaggaacatg    1020
tggcaggcct agggaccaaa gccatgaagg tttctgtggt cacagccatg tgctgcttct    1080
gggagggaca tctgctgccc tagttaagca tggtagtgag tgacaacttt gggttttcca    1140
atgcccacag caggaaccgg acctggcttt ataccctctg cctcccagag cattctgggc    1200
cagggtacca gaagggtcct cactgccgct tatatcctct ccctcctcc cacaggccat     1260 gctgtctaag aacacagtgg acagtggcca catggggatc ccaagcagga cagggctcaa    1320
ggctggagac agacttgtta aatcgtgcct gaggggaag gtatatgaca cctttgcaaa     1380
ctgggtaagt gaagagagga agtgtacgac agcccaacgg aagccccct ccccccagt      1440 actgtgaagc ctgtcaatcc cacaggggtg ggacttcggc ttacggtctc ctgcaaccag    1500
gacctttcac acacccacc cttctgcctg gtcatgtag ctgatcccag aggactagca      1560
ctttatgttt tcagtactga tggatggtaa gagacagcag aattgctgag ttatggagga    1620
ggcaaacaag acctcttcag aaacacagct aactaccac aagaccagaa ccaggctgtc     1680 cagaccctg cactggaaca tggagggatg gaacggtcag ggagggggc aggagcatgg      1740 ctaggatctg gcatgaggtg tgctgggcat agaaggagta ggggccccag gtaggttctg    1800
ggctcagaga aggcatgata gaagctagac acataagtca taatggcttt ctcatctggc    1860
cgggcagttt cgacgatgct tcagcatcca gcatttagg gatgtccagg gaacctctct     1920
gccacatcat agccgtgttc agttgtgagt aaggatcatc ctaaagagaa gcaccaagtg    1980
agcctacaga gaggacacag gtcacagtcg attcggagat gggaggtgtg tgtgtgtgtg    2040
tgtgtgtgtg tgtgtgtgtg tgtgtgtgta ccagcccttc tcaggttcta ggtaagaaag    2100
ggtgacttca aggcctttt taggggtcac tagttagagg tttgaaacat tctcttcccc    2160
catcactctt cagtatggaa atgggggaag agaatacata ggcctgatgt tagagttgga    2220
gtaggaaaga actaagaagt ggggttgaga gccatcagtt ctggcaggag acatgggtaa    2280
atcgactcag acttagtccc cccccccccc ccctgtctg aactcaatag ttgggatagg     2340
tgctcttaac tcataaagat tagtgagaag ttgaagctga cccaccatgg attcccatgt    2400
gttgggttat tctaagtagc catggctttt ttagtggcct ctgtgatctt ttctcgaaag    2460
ctaaatgggg agagctggca aaggatgttg gggactctgg gatccttgca tcccggagtg    2520
tacttcaaac atggaggtaa tgtaaaatgg agttaggtgc ctcctcagcc cagcaggcca    2580
cactgctcag tcagtctcat aagatggtgc ggctgctgtg gagggcggca tggagggtcc    2640
ccaaaaagtt atactcctgc ataaggccca gggattatt                           2679
```

<210> SEQ ID NO 3
<211> LENGTH: 29
<212> TYPE: DNA
<213> ORGANISM: Artificial Sequence
<220> FEATURE:
<223> OTHER INFORMATION: primer for PCR

<400> SEQUENCE: 3
tgtcactgcc acgccttctc ggtgcgcag                                       29

<210> SEQ ID NO 4
<211> LENGTH: 30
<212> TYPE: DNA
<213> ORGANISM: Artificial Sequence
<220> FEATURE:
<223> OTHER INFORMATION: primer for PCR

<400> SEQUENCE: 4

-continued

```
tcccggctgc cctttggccc atcttgtccc                    30

<210> SEQ ID NO 5
<211> LENGTH: 30
<212> TYPE: DNA
<213> ORGANISM: Artificial Sequence
<220> FEATURE:
<223> OTHER INFORMATION: primer for PCR

<400> SEQUENCE: 5
tgagaaagcg ttagacgctc tcagagccct                    30

<210> SEQ ID NO 6
<211> LENGTH: 4
<212> TYPE: PRT
<213> ORGANISM: Mus musculus

<400> SEQUENCE: 6

Ser Gly Leu Asp
 1

<210> SEQ ID NO 7
<211> LENGTH: 6
<212> TYPE: PRT
<213> ORGANISM: Mus musculus

<400> SEQUENCE: 7

Gly Asn Tyr Tyr Cys Cys
 1               5

<210> SEQ ID NO 8
<211> LENGTH: 6
<212> TYPE: PRT
<213> ORGANISM: Mus musculus

<400> SEQUENCE: 8

Gly Thr Arg Trp Ala Lys
 1               5

<210> SEQ ID NO 9
<211> LENGTH: 27
<212> TYPE: DNA
<213> ORGANISM: Artificial Sequence
<220> FEATURE:
<223> OTHER INFORMATION: primer for PCR

<400> SEQUENCE: 9
gaarrcatga aaggcctggc tggcgag                       27

<210> SEQ ID NO 10
<211> LENGTH: 30
<212> TYPE: DNA
<213> ORGANISM: Artificial Sequence
<220> FEATURE:
<223> OTHER INFORMATION: primer for PCR

<400> SEQUENCE: 10
gaattctcat gtcactgcca cgccttctcg                    30

<210> SEQ ID NO 11
<211> LENGTH: 27
<212> TYPE: DNA
<213> ORGANISM: Artificial Sequence
<220> FEATURE:
<223> OTHER INFORMATION: primer for PCR
```

```
<400> SEQUENCE: 11
ggatccaaga aaggcctggc tggcgag                               27

<210> SEQ ID NO 12
<211> LENGTH: 27
<212> TYPE: DNA
<213> ORGANISM: Artificial Sequence
<220> FEATURE:
<223> OTHER INFORMATION: primer for PCR

<400> SEQUENCE: 12
aagctttcat gtcactgcca cgccttc                               27

<210> SEQ ID NO 13
<211> LENGTH: 28
<212> TYPE: DNA
<213> ORGANISM: Artificial Sequence
<220> FEATURE:
<223> OTHER INFORMATION: primer for PCR

<400> SEQUENCE: 13
ggtaagctta tattgtttgc aactacct                              28

<210> SEQ ID NO 14
<211> LENGTH: 30
<212> TYPE: DNA
<213> ORGANISM: Artificial Sequence
<220> FEATURE:
<223> OTHER INFORMATION: primer for PCR

<400> SEQUENCE: 14
ggatcccatg tgacctaatg tttcatgtca                            30

<210> SEQ ID NO 15
<211> LENGTH: 30
<212> TYPE: DNA
<213> ORGANISM: Artificial Sequence
<220> FEATURE:
<223> OTHER INFORMATION: primer for PCR

<400> SEQUENCE: 15
tggtattctt atattgtttg caactaacta                            30

<210> SEQ ID NO 16
<211> LENGTH: 31
<212> TYPE: DNA
<213> ORGANISM: Artificial Sequence
<220> FEATURE:
<223> OTHER INFORMATION: primer for PCR

<400> SEQUENCE: 16
ggaaggccat gtgacctaat gtttcatgtc a                          31

<210> SEQ ID NO 17
<211> LENGTH: 10
<212> TYPE: DNA
<213> ORGANISM: Artificial Sequence
<220> FEATURE:
<223> OTHER INFORMATION: motif sequence

<400> SEQUENCE: 17
atgcttgccc                                                  10
```